(12) United States Patent
Katou

(10) Patent No.: US 10,285,682 B2
(45) Date of Patent: May 14, 2019

(54) MEDICAL DEVICE AND TREATMENT METHOD

(71) Applicant: TERUMO KABUSHIKI KAISHA, Shibuya-ku, Tokyo (JP)

(72) Inventor: Yukitoshi Katou, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 690 days.

(21) Appl. No.: 14/825,840

(22) Filed: Aug. 13, 2015

(65) Prior Publication Data

US 2015/0342592 A1   Dec. 3, 2015

Related U.S. Application Data

(63) Continuation of application No. PCT/JP2013/054098, filed on Feb. 20, 2013.

(51) Int. Cl.
*A61B 18/14*   (2006.01)
*A61B 17/02*   (2006.01)
(Continued)

(52) U.S. Cl.
CPC ...... *A61B 17/0218* (2013.01); *A61B 17/3478* (2013.01); *A61B 18/1445* (2013.01);
(Continued)

(58) Field of Classification Search
CPC .............. A61B 18/1492; A61B 18/149; A61B 18/1445; A61B 2018/00369;
(Continued)

(56) References Cited

U.S. PATENT DOCUMENTS

| 2004/0193147 A1 | 9/2004 | Malecki et al. |
| 2005/0101984 A1* | 5/2005 | Chanduszko ...... A61B 17/0057 606/185 |

(Continued)

FOREIGN PATENT DOCUMENTS

| JP | 2009-195717 A | 9/2009 |
| JP | 2009-254752 A | 11/2009 |
| JP | 2010-540198 A | 12/2010 |

OTHER PUBLICATIONS

International Search Report (PCT/ISA/210) dated Mar. 26, 2013, by the Japanese Patent Office as the International Searching Authority for International Application No. PCT/JP2013/054098.

*Primary Examiner* — Thomas A Giuliani
(74) *Attorney, Agent, or Firm* — Buchanan, Ingersoll & Rooney PC

(57) ABSTRACT

A medical device and treatment method are configured to form a hole as a passage, which is used for treatment, in biological tissues without puncturing the biological tissue and while reducing the influence on a living body The medical device includes: a shaft portion which is elongated, a pressing portion on a distal side of the shaft portion to press the tissue, and a thrusting portion provided further on the distal side of the shaft portion than the pressing portion and configured to be thrust into a joint portion of the tissue. When pressing the biological tissue using the pressing portion, a direction from the shaft portion to the pressing portion and a direction from the shaft portion to the thrusting portion are different from each other, and the pressing portion can be expanded and contracted in an expansion direction intersecting a shaft center direction of the shaft portion.

8 Claims, 22 Drawing Sheets

(51) Int. Cl.
*A61B 17/34* (2006.01)
*A61B 17/00* (2006.01)
*A61B 18/00* (2006.01)

(52) U.S. Cl.
CPC ...... *A61B 18/1492* (2013.01); *A61B 17/0057* (2013.01); *A61B 2017/00247* (2013.01); *A61B 2017/00575* (2013.01); *A61B 2018/0038* (2013.01); *A61B 2018/00351* (2013.01); *A61B 2018/141* (2013.01); *A61B 2018/144* (2013.01); *A61B 2018/1407* (2013.01); *A61B 2018/1425* (2013.01); *A61B 2018/1475* (2013.01)

(58) Field of Classification Search
CPC .. A61B 2018/00392; A61B 2018/1475; A61B 2018/0038; A61B 2018/00351; A61B 2018/1407; A61B 2018/141; A61B 2018/1425; A61B 2018/144; A61B 17/0218; A61B 17/3478; A61B 17/0057; A61B 2017/00247; A61B 2017/00575
USPC .................................... 606/41, 185
See application file for complete search history.

(56) References Cited

U.S. PATENT DOCUMENTS

| | | |
|---|---|---|
| 2009/0093802 A1 | 4/2009 | Kulesa et al. |
| 2009/0093803 A1* | 4/2009 | Herrin ................ A61B 18/1492 606/33 |
| 2012/0179188 A1 | 7/2012 | Chanduszko et al. |

* cited by examiner

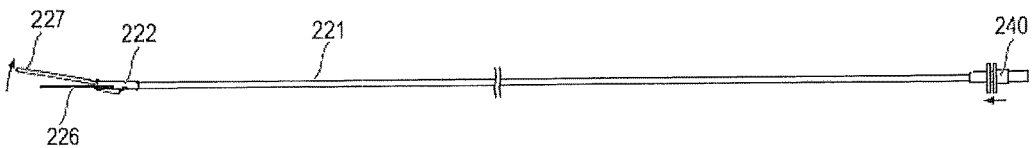
Fig. 35(A)
Fig. 35(B)
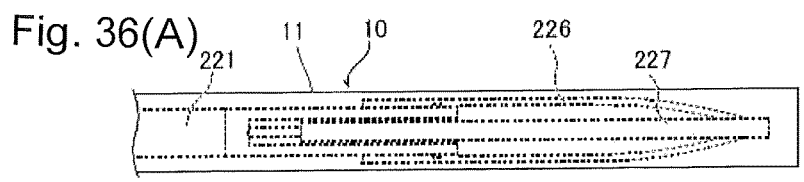
Fig. 36(A)
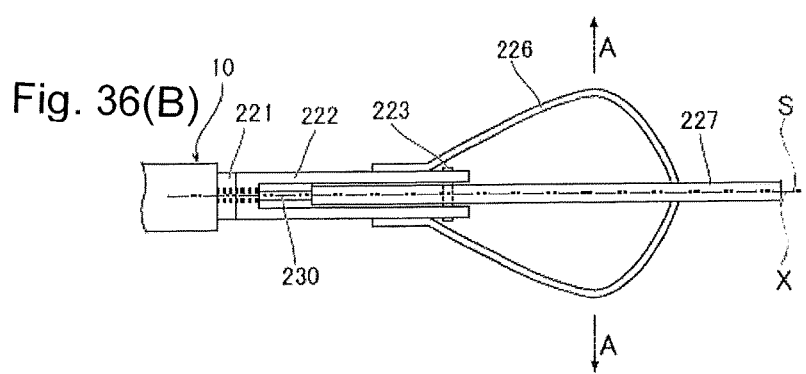
Fig. 36(B)

MEDICAL DEVICE AND TREATMENT METHOD

CROSS-REFERENCES TO RELATED APPLICATIONS

This application is a continuation of International Application No. PCT/JP2013/054098 filed on Feb. 20, 2013, the entire content of which is incorporated herein by reference.

TECHNICAL FIELD

The present invention generally relates to a medical device and a treatment method, and particularly to a medical device to be inserted into lumens, and a treatment method.

BACKGROUND DISCUSSION

In recent years, treatment using a percutaneous surgical procedure with a catheter has been performed for treating the heart. The percutaneous surgical procedure with a catheter is minimally invasive, and therefore, is considered a desirable method if the technique can obtain the same effect as that of open heart surgery.

Examples of the treatment using the percutaneous surgical procedure with a catheter include treatment of atrial fibrillation, mitral valve repair, mitral valve replacement, left atrial appendage closure, and the like. In the atrial fibrillation, the atria enter a state of convulsion due to a state in which a disorderly electrical signal is frequently in the atria, and it has been known that abnormal automaticity occurring in a joint portion between the left atrium and the pulmonary vein is a primary cause of atrial fibrillation. For this reason, it has been known that it is effective to ablate (cauterize) abnormal automaticity by using an ablation catheter to reach the left atrium.

The mitral valve repair is performed in order to repair the mitral valve when there is damage or the like in the mitral valve, which is positioned between the left atrium and the left ventricle and suppresses the backflow of blood. In the mitral valve repair, the mitral valve is repaired through a catheter after the catheter reaches the left atrium. Similarly to the mitral valve repair, the mitral valve replacement is performed in order to replace the mitral valve with an artificial valve when there is damage or the like in the mitral valve. In the mitral valve replacement, the mitral valve is replaced with an artificial valve through a catheter after the catheter reaches the left atrium.

The left atrial appendage closure is performed in order to suppress the generation of thrombi by preventing the accumulation of blood in the left atrial appendage, and to thereby prevent an occurrence of cerebral infraction or the like due to the thrombi. In the left atrial appendage closure, the left atrial appendage is occluded by indwelling a wire or the like in the left atrial appendage through a catheter after the catheter reaches the left atrium.

In each of the above-described treatments, it is necessary to make a catheter reach the left atrium. As a method for this, a method, for example, a brockenbrough method or the like, has been known (for example, refer to U.S. Application Publication No. 2012/0179188) in which a hole is opened by piercing the atrial septum with a needle after making a catheter percutaneously reach the right atrium through the femoral vein or the like, and then, the catheter is made to reach the left atrium side through this hole.

However, when a hole is opened by puncturing the atrial septum as described above, there is a high risk of cyanosis or cardiac hypertrophy caused by blood flowing into the right atrium from the left atrium after treatment, depending on the size of the hole. Therefore, in some cases, treatment is required for occluding the hole in order to reduce the risk thereof. Particularly, in the mitral valve repair or mitral valve replacement, it is necessary to pass through a formed hole a catheter which has a comparatively larger diameter in order to accommodate a device for repairing the mitral valve, an artificial valve, or the like, therefore, the necessity to occlude the hole increases. As the method of occluding a hole, for example, a method has been known in which a hole is occluded using an occlusive instrument or the like which is indwelled in the hole by being enlarged in a disk shape on both sides of the left atrium and the right atrium. However, if such an occlusive instrument is attached to the hole, in a case where, for example, it is necessary to perform the same treatment again, there is a possibility that it may not be easy to perform the re-treatment due to the occlusive instrument inhibiting access of the catheter to the left atrium. In addition, such an occlusive instrument is a foreign material to a living body and easily forms thrombi.

In addition, when opening a hole in the atrial septum through the aforesaid puncturing, since the aorta is positioned in the vicinity of the septum primum, there is a possibility that the aorta may be punctured, which is the base of blood circulation to the entire body, due to the puncturing of the septum primum.

SUMMARY

A medical device is disclosed which can form a hole as a passage, which is used for treatment, on biological tissue without puncturing the biological tissues and while reducing the influence on a living body, when the passage to a treatment region to be treated is occluded by a joint region of the biological tissues.

The medical device includes: a shaft portion which is elongated and possesses a central axis; a pressing portion on a distal side of the shaft portion and configured to press the biological tissue; and a thrusting portion provided further on the distal side of the shaft portion than the pressing portion and configured to be thrust into a joint portion of the biological tissue while the tissue is being pressed by the pressing portion. The pressing portion and the thrusting portion are configured so that when pressing the biological tissues using the pressing portion, a direction from the shaft portion to the pressing portion and a direction from the shaft portion to the thrusting portion are different from each other, and at least one of the pressing portion and the thrusting portion can be expanded and contracted in an expansion direction intersecting a shaft center direction of the shaft portion.

The medical device having the aforesaid configuration can contract at least one of the pressing portion and the thrusting portion and move it to a predetermined place within the body lumen. Moreover, since the direction from the shaft portion to the pressing portion and the direction from the shaft portion to the thrusting portion are different from each other when pressing the biological tissues using the pressing portion, the medical device can efficiently separate the joint portions from one another by thrusting the thrusting portion into the joint portion of the biological tissues which are positioned in a direction different from a region to be pressed while pressing the biological tissues using the pressing portion. Therefore, it is possible to perform treatment through a hole which is formed by separating the joint portions from one another without puncturing the biological tissues and while reducing the influence on the living body. In addition, the pressing portion and the thrusting portion may be formed of the same member as each other or different members from each other. Here, the fact that the pressing portion and the thrusting portion are formed of the same member as each other indicates that the pressing portion and the thrusting portion exist as a portion with the same member as each other, that is, the pressing portion and the thrusting portion are interlocked with each other so as not to be separated from each other, and the distal end of the shaft portion and the thrusting portion are not interlocked with each other. In addition, the fact that the pressing portion and the thrusting portion are formed of different members from each other indicates that the pressing portion and the thrusting portion are not portions with the same member as each other, that is, the pressing portion and the thrusting portion are separated from each other and each of the pressing portion and the thrusting portion is interlocked with the distal end of the shaft portion.

If the pressing portion and the thrusting portion are made to be formed of an elastically deformable wire, it is possible to relatively easily contract and expand the pressing portion and the thrusting portion and to reduce the size of the device due to its simple configuration. Thus, the insertion of the device into the body lumen becomes easier.

When the pressing portion is made to be positioned away from the shaft center of the shaft portion when being projected onto a reference surface which is orthogonal to the expansion direction of the pressing portion and passes through the shaft center of the shaft portion, it is possible to effectively press the biological tissues using the pressing portion since the shaft portion hardly comes into contact with the biological tissues with which the pressing portion comes into contact.

When the pressing portion and the thrusting portion can be opened and closed so as to approach and be separated from each other through an operation of the shaft portion on the proximal side, it is possible to exert force on biological tissues, which are joined together, in a direction in which the biological tissues are separated from each other by the pressing portion and the thrusting portion. Therefore, it is possible to effectively separate the joint portions from one another.

When the pressing portion and the thrusting portion can take a form in which the direction from the shaft portion to the pressing portion is the same as the direction from the shaft portion to the thrusting portion when the biological tissues are not pressed by the pressing portion, it is possible to differentiate the direction from the shaft portion to the pressing portion from the direction from the shaft portion to the thrusting portion only when the biological tissues are pressed by the pressing portion.

The pressing portion can be configured to come into contact with the foramen ovale valve on the right atrium side and press the foramen ovale valve to the left atrium side and the thrusting portion is made to be thrust between the foramen ovale valve and the atrial septum, so as to form a foramen ovale, it is possible to effectively separate the foramen ovale valve from the atrial septum and to easily form a foramen ovale which is configured such that the foramen ovale valve overlaps the atrial septum, by thrusting the thrusting portion into the joint portion between the atrial septum and the foramen ovale valve on which tensile force is exerted in a direction away from each other while pressing and moving the foramen ovale valve in a direction away from the atrial septum using the pressing portions.

In addition, a hole can be formed which allows access between the left atrium and the right atrium without puncturing the atrial septum through a treatment method that includes forming a foramen ovale by separating the foramen ovale valve and the atrial septum from each other using a medical device which is percutaneously inserted into the right atrium.

The treatment method preferably further includes a treatment process in which treatment is performed by percutaneously inserting a treatment instrument that performs treatment into the left atrium from the right atrium through the foramen ovale, after the separation process, it is possible to perform treatment on the left atrium side through the foramen ovale without puncturing the atrial septum and while reducing the influence on a living body. After the treatment, since the pressure on the left atrium side usually exceeds the pressure on the right atrium side, the valve-like hole is in a closed state. Therefore, prevention of communication between the atria can be expected.

The treatment method can also involve joining the foramen ovale valve and the atrial septum after the treatment by sandwiching the foramen ovale valve and the atrial septum using an electrode, applying electrical energy to the electrode, and joining the foramen ovale valve and the atrial septum together This makes it possible to occlude the foramen ovale without attaching an occlusive instrument, which is a foreign material to a living body and can be a factor of forming thrombi, to the foramen ovale. In addition, in a case where it is necessary to access the left atrium from the right atrium again to perform treatment, it is possible to reduce interference on the treatment since no occlusive instrument is attached to the foramen ovale.

The medical device includes a shaft portion which is elongated; a pressing portion which is provided on a distal side of the shaft portion; and a thrusting portion which is provided further on the distal side of the shaft portion than the pressing portion. When pressing biological tissues using the pressing portion, a direction from the shaft portion to the pressing portion and a direction from the shaft portion to the thrusting portion are different from each other. At least one of the pressing portion and the thrusting portion can be expanded and contracted in an expansion direction intersecting a shaft center direction of the shaft portion. The treatment method further includes an expansion process in which the pressing portion and the thrusting portion are expanded by making the pressing portion and the thrusting portion protrude from a distal end of a tubular body after making the medical device, which is in a state where at least one of the pressing portion and the thrusting portion is contracted, reach the inside of the right atrium through the inside of the tubular body that is percutaneously inserted into the right atrium. When a foramen ovale is formed by thrusting the thrusting portion into a joint portion between the foramen ovale valve and the atrial septum while pressing the foramen ovale valve to the left atrium side using the pressing portion in the separation process, it is possible to move the pressing portion and the thrusting portion within the body lumen through the tubular body in a state where the pressing portion and the thrusting portion are contracted, and to expand the pressing portion and the thrusting portion in the right atrium. Furthermore, the thrusting portion is thrust into the joint portion between the atrial septum and the foramen ovale valve on which tensile force is exerted in a direction away from each other while pressing and moving the foramen ovale valve in a direction away from the atrial septum using the pressing portion. By doing this, the foramen ovale valve is effectively separated from the atrial septum and a foramen ovale can be easily formed which is configured such that the foramen ovale valve overlaps the atrial septum.

The pressing portion and the thrusting portion can be formed of a common member, whereby pressing and thrusting can be performed in a state where the pressing portion and the thrusting portion are interlocked with each other so as not to be separated from each other.

The treatment method can include different members forming the pressing portion and the thrusting portion, whereby pressing and thrusting can be performed in a state where the pressing portion and the thrusting portion are separated from each other.

The pressing portion and the thrusting portion can be formed of an elastically deformable wire, which makes it possible to rather easily contract and expand the pressing portion and the thrusting portion and to reduce the size of the device due to its simple configuration. Thus, the insertion of the device into the body lumen becomes easier.

In the treatment method, if the pressing portion is made to be positioned away from the shaft center of the shaft portion when being projected onto a reference surface which is orthogonal to the expansion direction of the pressing portion and passes through the shaft center of the shaft portion, it is possible to effectively press the biological tissues using the pressing portion since the shaft portion hardly comes into contact with the biological tissues with which the pressing portion comes into contact.

If the pressing portion and the thrusting portion can be opened and closed so as to approach and be separated from each other through an operation of the shaft portion on the proximal side and are made to be opened and closed in the separation process, it is possible to exert force on biological tissues, which are joined together, in a direction in which the biological tissues are separated from each other by the pressing portion and the thrusting portion. Therefore, it is possible to effectively separate the joint portions from one another.

In the separation process, if the pressing portion and the thrusting portion can take a form in which the direction from the shaft portion to the pressing portion and the direction from the shaft portion to the thrusting portion are the same as each other when the biological tissues are not pressed by the pressing portion, it is possible to differentiate the direction from the shaft portion to the pressing portion from the direction from the shaft portion to the thrusting portion only when the biological tissues are pressed by the pressing portion.

Another aspect of the disclosure here involves a medical device for forming a foramen ovale in biological tissue in a living body. The device comprises: an elongated shaft portion configured to be introduced into a living body and possessing a distal end to be introduced into a right atrium in the living body that is separated from a left atrium by a foramen ovale valve and an atrial septum, wherein the shaft portion possessing a central axis; a pressing portion configured to press the biological tissue, with the pressing portion being mounted on a distal side of the shaft portion so that the pressing portion and the shaft portion move together; and a thrusting portion configured to be thrust into a joint portion between the foramen ovale valve and the atrial septum while the biological tissue is pressed by the pressing portion, with the thrusting portion being mounted on a distal side of the shaft portion so that the thrusting portion and the shaft portion move together, and with the thrusting portion possessing a distal end located distal of a distal-most part of the pressing portion. The pressing portion and the thrusting portion are configured so that a direction from the shaft portion to the pressing portion and a direction from the shaft portion to the thrusting portion are different from one another when the pressing portion is pressing the biological tissue. In addition, at least one of the pressing portion and the thrusting portion is expandable outwardly and contractable inwardly in a direction transverse to the central axis the shaft portion.

BRIEF DESCRIPTION OF THE DRAWINGS

FIGS. 2(A) and 2(B) are plan views showing a medical device according to a first embodiment, in which FIG. 2(A) shows a long sheath and FIG. 2(B) shows a long instrument.

FIGS. 5(A) and 5(B) are plan views showing the long instrument and the long sheath in the first embodiment, in which FIG. 5(A) shows a state when a distal end deformation portion of the long instrument is accommodated in the long sheath and FIG. 5(B) shows a state when a distal end deformation portion of the long instrument protrudes from the long sheath.

FIG. 8 is a cross-sectional view of a distal portion of a catheter taken along the section line 9-9 in FIG. 8.

FIGS. 15(A) and 15(B) are plan views showing a hand-side operating unit when moving a slide portion, in which FIG. 15(A) shows a state during a slide movement and FIG. 15(B) shows a state after the slide movement.

FIGS. 16(A)-16(C) are plan views showing an operation state of positioning and holding means, in which FIG. 16(A) shows a state before the operation, FIG. 16(B) shows a state when a needle positioning portion is operated, and FIG. 16(C) shows a state when a holding portion is operated.

FIGS. 32(A) and 32(B) are views showing a distal portion of a long instrument in a second embodiment, in which FIG. 32(A) is a plan view and FIG. 3(B) is a side view when viewed from the arrow 32 in FIG. 32(A).

FIGS. 33(A) and 33(B) are plan views showing the long instrument and a long sheath in the second embodiment, in which FIG. 33(A) shows a state when a distal end deformation portion of the long instrument is accommodated in the long sheath and FIG. 33(B) shows a state when the distal end deformation portion of the long instrument protrudes from the long sheath.

FIGS. 35(A) and 35(B) are plan views showing a long instrument in a third embodiment, in which FIG. 35(A) shows a state when a pressing portion and a thrusting portion are closed and FIG. 35(B) shows a state when the pressing portion and the thrusting portion are opened.

FIGS. 36(A) and 36(B) are plan views showing the long instrument and a long sheath in the third embodiment, in which FIG. 36(A) shows a state when the long instrument is accommodated in the long sheath and FIG. 36(B) shows a state when the long instrument protrudes from the long sheath.

FIGS. 37(A) and 37(B) are plan views showing a distal portion of the long instrument in the third embodiment, in which FIG. 37(A) shows a state when the pressing portion and the thrusting portion are closed and FIG. 37(B) shows a state when the pressing portion and the thrusting portion are opened.

FIGS. 39(A) and 39(B) are plan views showing a long instrument in a fourth embodiment, in which FIG. 39(A) shows a state before a rotary operation is performed and FIG. 39(B) shows a state when the rotary operation has been performed.

DETAILED DESCRIPTION

Figure 1:
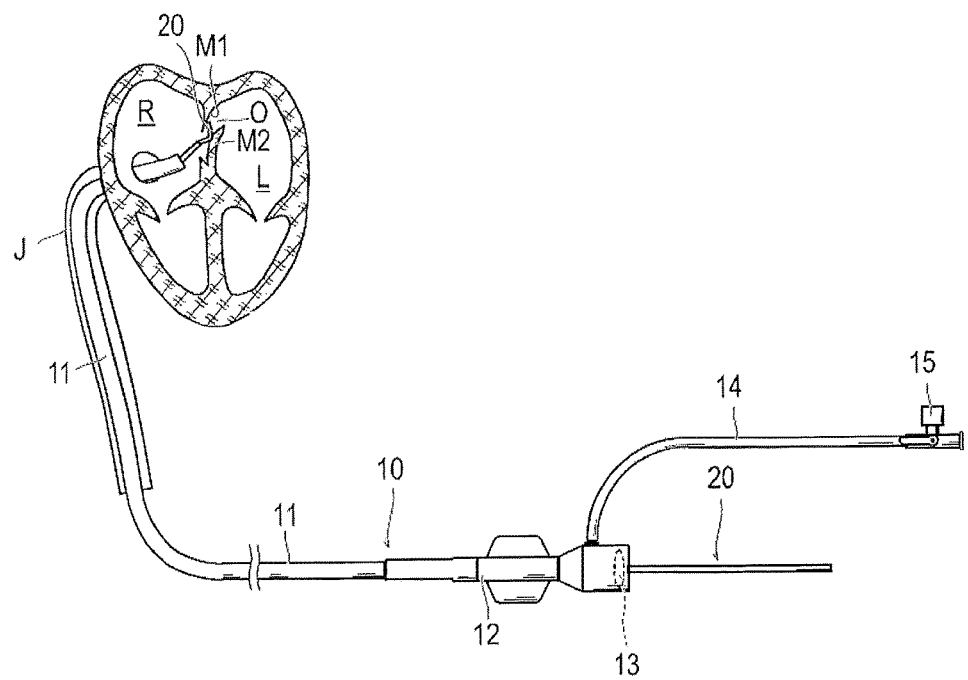
FIG. 1 is a schematic cross-sectional view showing the vicinity of the heart septum and a foramen ovale of the heart.

Hereinafter, embodiments of the medical device, representing examples of the invention disclosed here, will be described with reference to the accompanying drawings. Note that in some cases, dimensional ratios in the drawings are exaggerated and are different from the actual ratios for the convenience of description.

First Embodiment

The medical device according to a first embodiment disclosed here performs treatment on a left atrium L side by separating the septum primum (hereinafter, referred to as the foramen ovale valve) M2, which is joined to the septum secundum (hereinafter, referred to as the atrial septum) M1 of the heart, to form a foramen ovale O, and a treatment instrument 30 which is percutaneously inserted into the right atrium R is introduced into the left atrium L side through the formed foramen ovale O. Note that the "formation of a foramen ovale O" includes a case in which a foramen ovale O is formed so as to be enlarged from a state where a space between the right atrium R and the left atrium L is partially occluded, as well as a case where the foramen ovale O is formed which passes through the space between the right atrium R and the left atrium L from a state where the space between the right atrium R and the left atrium L is completely occluded. In addition, the term "separation" means that tissues which are joined together are separated from each other and does not depend on the place, the size, and the shape of the tissues, the separation method, and the like.

Figure 6:
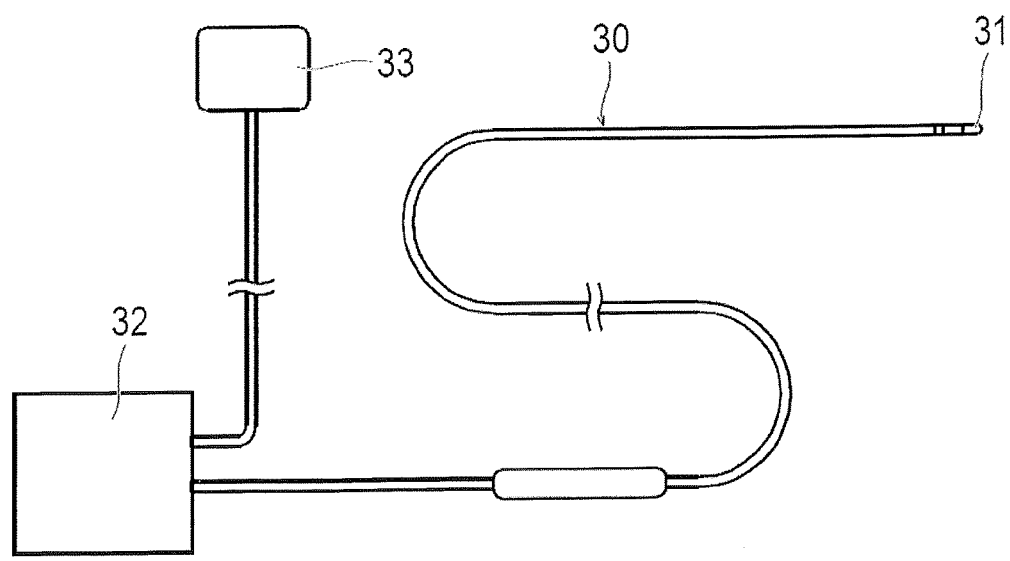
FIG. 6 is a plan view showing a treatment instrument of the medical device according to the first embodiment.

As shown in FIGS. 1 and 2, the medical device according to the first embodiment includes a long sheath 10 (tubular body) and a long instrument 20 which can be accommodated in the long sheath 10 and is used for forming the foramen ovale O. Furthermore, the medical device includes a treatment instrument 30 (refer to FIG. 6) which is used for performing treatment by being inserted into the left atrium L from a right atrium R side through the foramen ovale O which is formed by the long instrument 20, and a closing device 40 (refer to FIG. 7) which joins the atrial septum M1 and the foramen ovale valve M2 together using electrical energy after completion of the treatment using the treatment instrument 30. Note that, in the description below, the hand side of the device will be referred to as a "proximal side" (proximal end) and the side through which the device is inserted into the living body will be referred to as a "distal side" (distal end). In addition, in the drawing, "L" represents the left atrium and "R" represents the right atrium. In addition, the treatment instrument 30 in FIG. 6 is an ablation catheter. However, the treatment instrument is not limited to an ablation catheter and also includes a treatment catheter such as a balloon catheter or the like. Here, the term "catheter" represents a catheter that includes a tubular body which is used for medical purposes.

The foramen ovale O enables left-to-right shunting of blood in the heart in a fetal stage. The foramen ovale is positioned at the atrial septum M1 of the heart and is occluded and closed in a manner in which the foramen ovale valve M2 overlaps the atrial septum M1. In general, since the foramen ovale valve M2 is joined to the atrial septum M1 in adulthood, the foramen ovale O is completely or partially closed. The medical device according to the first embodiment forms the foramen ovale O again and uses the foramen ovale O in order to introduce the treatment instrument 30, which has been percutaneously inserted into the right atrium R, into the left atrium L. Note that in a case where the foramen ovale O is not closed, the foramen ovale O is closed by the foramen ovale valve M2 due to the pressure of the left atrium L exceeding the pressure on the right atrium R side in an ordinary heart. However, when the pressure on the right atrium R side exceeds the pressure on the left atrium L side under tension (for example, when coughing or standing firm) or the like, the foramen ovale valve M2 is opened on the left atrium L side, and therefore, blood flows into the left atrium L side (artery side) from the right atrium R side (venous side). If thrombi are included in blood, the thrombi move from the venous side to the artery side and flow from the left atrium, the left ventricle, the aorta, and the brain in this order, thereby possibly becoming a factor of a stroke, a migraine headache, or the like. Accordingly, in the present embodiment, the foramen ovale O is closed by the closing device 40 after treatment in the left atrium L is completed. Note that, as described above, the foramen ovale O is closed due to the pressure of the left atrium L exceeding the pressure on the right atrium R side. Therefore, influence on a living body is smaller than a case where a hole is formed in the atrial septum M1 through a brockenbrough method or the like, depending on the conditions such as the size of the hole or the like.

Figure 2A:
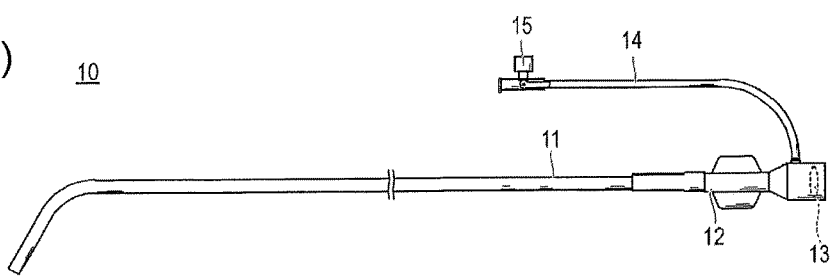

As shown in FIG. 2(A), the long sheath 10 includes a tubular sheath portion 11 which is introduced into the right atrium R by being inserted through the femoral vein or the like; a hub portion 12 which is provided in a proximal end of the sheath portion 11; a valve body 13 which is provided in the hub portion 12; a side port 14 which is connected to the hub portion 12; and a three-way stopcock 15 which is provided in the side port 14. The sheath portion 11 is made such that the long instrument 20, the treatment instrument 30, and the closing device 40 can be inserted into the sheath portion 11. The valve body 13 plays a role in inserting the long instrument 20, the treatment instrument 30, and the closing device 40 into the sheath portion 11 while retaining liquid-tightness. The side port 14 can be used for priming in the long sheath 10 or for injecting a contrast agent, a drug, or the like thereinto.

Figure 2B:
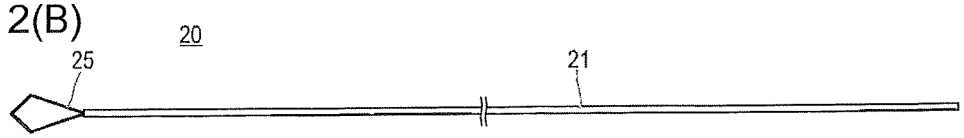
Figure 3:
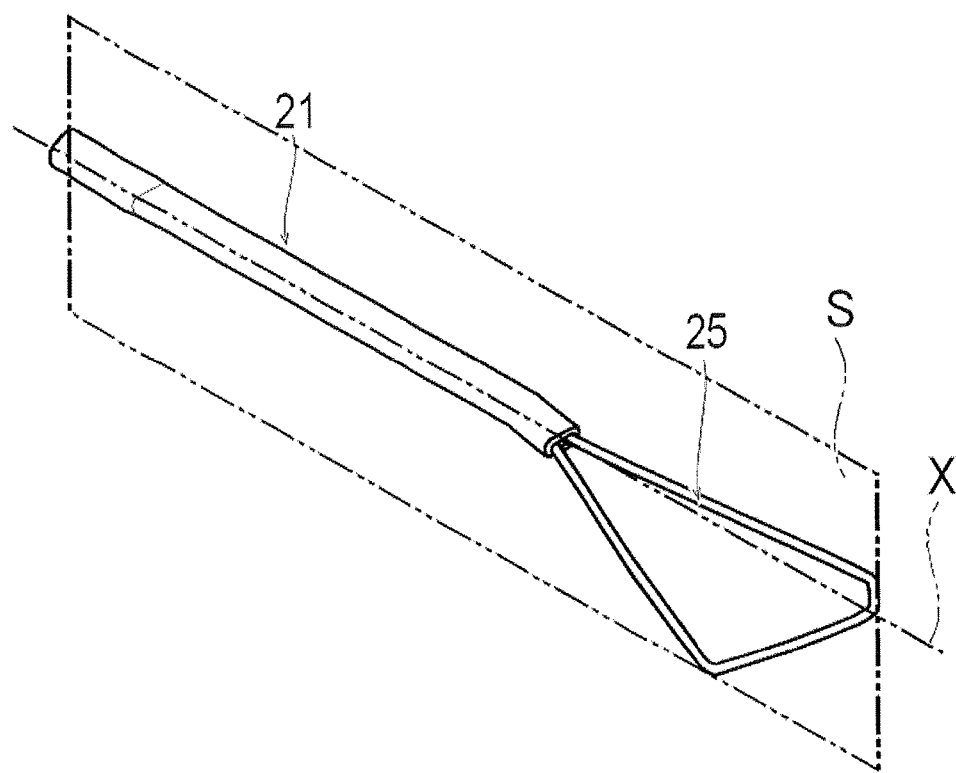
FIG. 3 is a perspective view showing a distal portion of the long instrument in the first embodiment.
Figure 4:
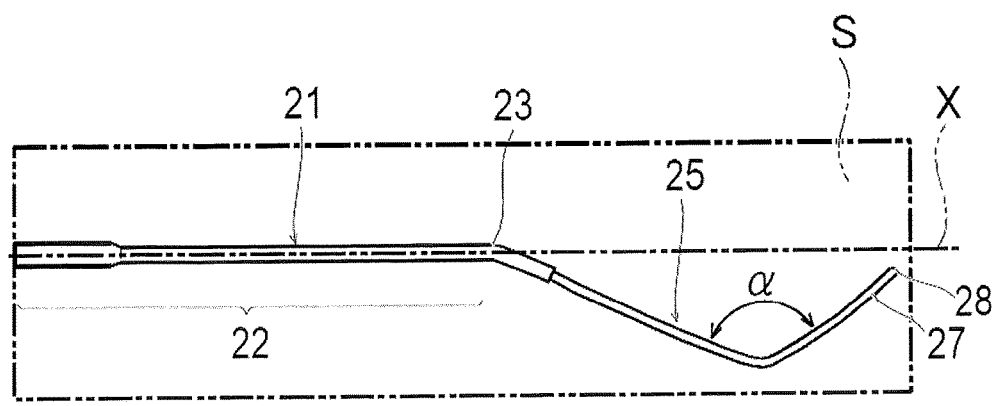
FIG. 4 is a plan view showing the distal portion of the long instrument in the first embodiment.
Figure 5A:
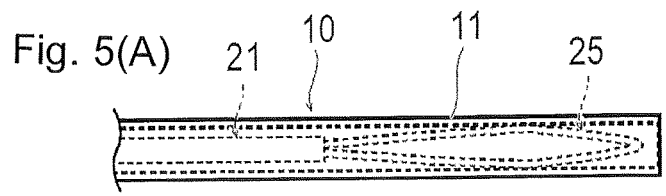
Figure 5B:
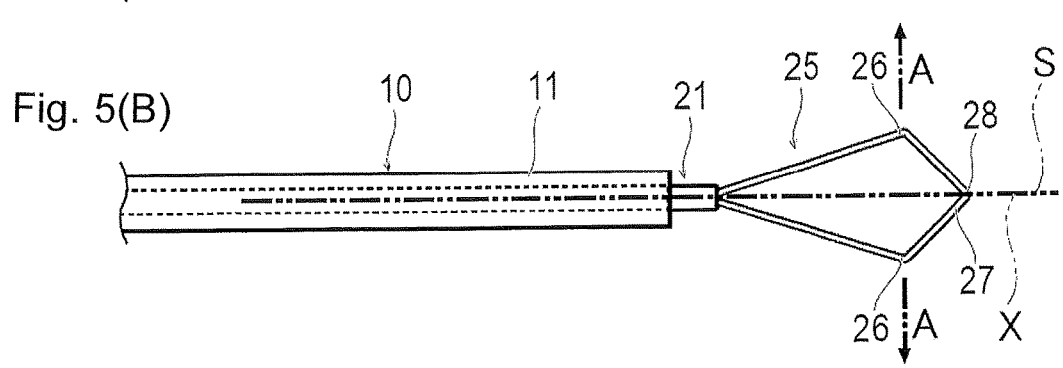

As shown in FIG. 2B, the long instrument 20 includes a shaft portion 21 which is elongated; and a distal end deformation portion 25 which is provided on a distal side of the shaft portion 21 and can be accommodated in the long sheath 10 by being elastically contracted. The distal end deformation portion 25 is annularly formed (i.e., in the shape of a closed loop in the illustrated embodiment) of an elastic material as shown in FIGS. 3 to 6, and has two pressing portions 26 which expand in an expansion direction A intersecting or transverse to a shaft center (central axis of the shaft) X direction of the shaft portion 21 by protruding and being exposed from the long sheath 10. That is, the pressing portions 26 expand outwardly from, or transversely away from, the shaft center axis X when seen in plan view such as shown in FIG. 5(B). The distal end deformation portion 25 also has or includes a thrusting portion 27 which is positioned further on a distal side than the pressing portions 26 in a direction, different from a direction from the shaft portion 21 to the pressing portions 26 as shown in FIG. 5. That is, the direction from the pressing portions 26 to the thrusting portion 27 is different from a direction from the shaft portion 21 to the pressing portions 26 in plan view as shown in FIG. 5(B). The pressing portion 26 is positioned at a distal portion of the shaft portion 21 away from the shaft center (central axis of the shaft) X of the shaft portion 21 due to the formation of a shaft bent portion 23 which is formed so as to be bent in a direction away from the shaft center (central axis of the shaft) X of the main portion 22, which is formed in a linear shape or a substantially linear shape, of the shaft portion 21 as shown in FIG. 4, when projected onto a reference surface S which is orthogonal to the expansion direction A and passes through the shaft center (central axis of the shaft) X of the shaft portion 21 (the distal portion of the shaft portion 21 appears on, or is present in, the reference surface S as shown in FIG. 4 side view. In addition, a most distal portion 28 of the distal end deformation portion 25 is positioned substantially on an extension line of the shaft center X of the shaft portion 21 as shown in FIG. 5(A. That is, a plane containing the axis X and perpendicular to the plane of the paper depicting FIG. 5 also passes through the most distal portion 28. When the shape of the distal end deformation portion 25 is projected onto the reference surface S, the pressing portion 26 is formed further on the distal side than the shaft bent portion 23 and is bent to a side which is opposite to the shaft bent portion 23. That is, the direction in which the shaft bent portion 23 is bent relative to the shaft portion 21 (the direction of bending from the shaft portion 21 to the pressing portion 26 as shown in FIG. 4) is opposite to the direction in which the thrusting portion 27 is bent relative to the shaft bent portion 23 (the direction of bending from the pressing portion 26 to the most distal portion 28 as shown in FIG. 4). The bending angle α in the pressing portion 26 is preferably 90 degrees to 150 degrees, but the present invention is not limited to this angular range. Note that the distal end deformation portion 25 is formed in a symmetrical shape with respect to the reference surface S, but may not necessarily be in the symmetrical shape. Note that, in the present embodiment, the pressing portion 26 and the thrusting portion 27 are formed of the same member as each other and exist as a portion formed of the same member as each other. Here, the fact that the pressing portion and the thrusting portion are formed of the same member as each other indicates that the pressing portion and the thrusting portion exist as a portion with the same member as each other, that is, the pressing portion and the thrusting portion are interlocked with each other so as not to be separated from each other, and the distal end of the shaft portion and the thrusting portion are not directly interlocked with each other (the pressing portion 26 exists between the shaft portion 21 and the thrusting portion 27 as shown FIG. 4).

The distal end deformation portion 25 is made into an elastically deformable wire formed of, for example, a NiTi alloy or the like which is a superelastic material. The shaft portion 21 is formed by, for example, a metal tube, such as stainless steel or the like, and a tube which is formed of resin and a reinforcing material made of metal. The distal end deformation portion 25 is fixed to the shaft portion by caulking the shaft portion in a state where the wire constituting the distal end deformation portion 25 is inserted into the shaft portion. Note that the shaft portion 21 preferably has flexibility to the extent that the shaft portion can move in the curved long sheath 10 and preferably has rigidity to the extent that the distal end deformation portion 25, which is fixed to the distal end of the shaft portion can be pressed to (against) biological tissues M (generic term of M1 and M2). In addition, the shaft portion 21 may not be in a tubular shape. In addition, a method of joining the shaft portion 21 and the distal end deformation portion 25 together is not particularly limited. For example, the shaft portion 21 and the distal end deformation portion 25 may be integrally formed.

The treatment instrument 30 for performing treatment by being inserted into the left atrium L from the right atrium R through the foramen ovale O is, for example, an ablation catheter for ablating (cauterizing) abnormal automaticity in a joint portion between the left atrium L and the pulmonary vein, as shown in FIG. 6. The ablation catheter includes an electrode 31 for ablation at a distal portion, is connected to a high-frequency generation device 32 for supplying an electric current to the electrode 31, and is used together with a body surface counter electrode 33 which is attached to the body surface of a patient and forms a pair with the electrode 31. Since the ablation catheter has a general known configuration, the detailed description of the ablation catheter will not be repeated.

Note that the treatment instrument 30 is not limited to the ablation catheter as long as the treatment instrument is used by being inserted to the left atrium L side from the right atrium R side, and for example, a catheter or the like may be used which is used in mitral valve repair, mitral valve replacement, left atrial appendage closure, or the like. In addition, the treatment instrument 30 may not be necessarily provided. Note that the treatment in the present specification is not limited to treatment which is performed for therapy, and for example, also includes treatment or the like for observation. The therapy is intended to treat, cure, alleviate, relieve, change, meliorate, ameliorate, recover, improve, or act a disease or a symptom of a patient.

Figure 7:
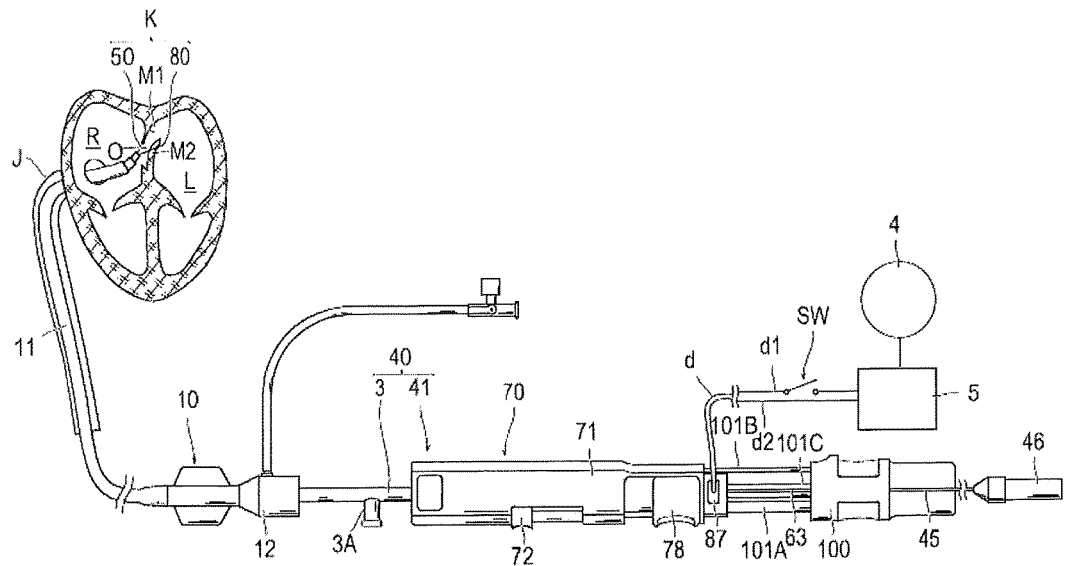
FIG. 7 is a plan view showing a closing device of the medical device according to the first embodiment.
Figure 8:
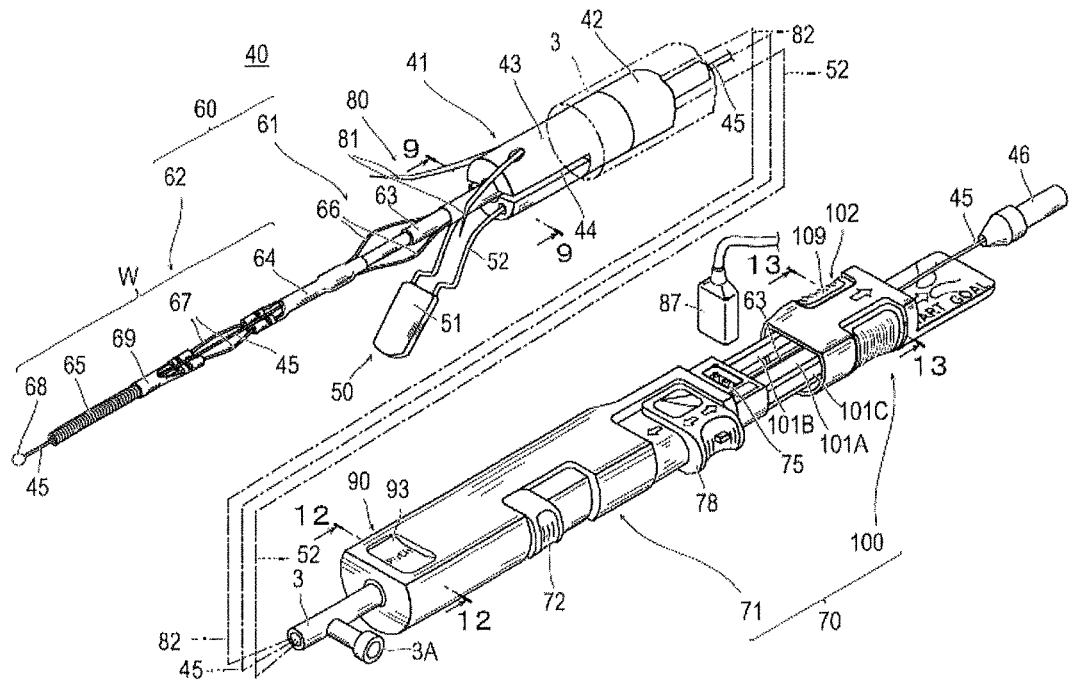
FIG. 8 is a perspective view showing a closing device of the medical device according to the first embodiment.

As shown in FIGS. 7 and 8, the closing device 40 is a device that closes the foramen ovale O by joining the atrial septum M1 and the foramen ovale valve M2 of the heart together using electrical energy. Note that FIG. 8 is illustrated in a state in which only a hand-side operating unit 70 is reduced for the convenience of description.

The closing device 40 has a catheter 41 which is constituted such that the hand-side operating unit 70 is attached to a proximal end of a catheter main body 42; a guiding sheath 3 of which the proximal end can be interlocked with the hand-side operating unit 70 and into which the catheter main body 42 can be inserted; and energy supply means 4 which supplies electrical energy for fusing or necrotizing a biological tissue M. The catheter 41 includes a clamping means K for sandwiching the foramen ovale valve M2 and the atrial septum M1, in the distal portion of the catheter main body 42; and a positioning and holding means 60 for holding or positioning of the biological tissue M in order to stably or accurately perform the surgical procedure with the clamping means K, in the distal portion of the catheter main body 42.

When using the closing device 40, the guiding sheath 3 is first inserted into the long sheath 10, which has been inserted through the femoral vein. The guiding sheath 3 is inserted into the long sheath 10 in a state where the clamping means K, which is provided at a distal end of the catheter main body 42, and the catheter main body 42 are accommodated in the inside of the guiding sheath. After the distal end reaches the region of the heart at which the surgical procedure is to be performed, the clamping means K is made to protrude from the catheter main body 42 by operating the hand-side operating unit 70. The tissues of the atrial septum M1 and the foramen ovale valve M2 of the heart in which a foramen ovale O is formed are then sandwiched by the clamping means K. In this sandwiched state, the clamping means K is supplied with electrical energy, both the tissues are heated and fused, and the defect O is closed. That is, the clamping means K functions as a heating unit.

Figure 9:
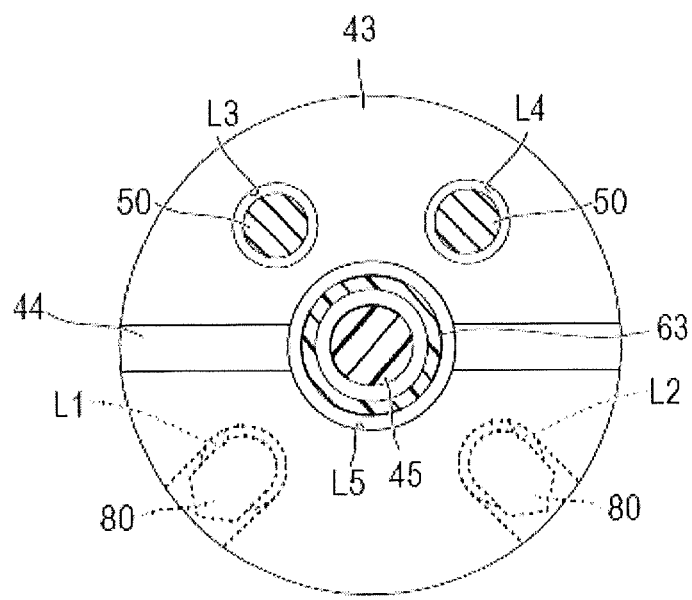

The clamping means K is constituted of a sandwich portion 50 which comes into direct contact with one side surface of the atrial septum M1; and a needle portion 80 with which the foramen ovale valve M2 is pierced. The sandwich portion 50 includes a flat plate portion 51 with an overall flat plate shape; and a pair of wire portions 52 connected to the proximal portion of the flat plate portion 51. A distal end tip 43 is adhered and fixed to the distal end of the catheter main body 42, and as shown in FIG. 9, the position of the flat surface of the sandwich portion 50 is restricted by lumens L3 and L4 which are formed so as to be in communication with the catheter main body 42 and the distal end tip 43. In addition, a groove portion 44 is formed at the distal end tip 43 so as to be cut from the distal side.

The distal sides of the wire portions 52 are bent. When the wire portions 52 are drawn into the lumens L3 and L4, as shown in FIGS. 10 and 11, the curves of the wire portions 52 extend and elastically deform in a shape similar to a straight line, and the flat plate portion 51 which is provided further on the distal side than the wire portion 52 moves to the needle portion 80 side (i.e., the flat plate portion 51 moves toward the needle portion 80).

In contrast, the needle portion 80 includes two needle distal portions 81 which are held in the distal end tip 43; and two needle proximal portions 82 which are provided so as to extend from the proximal side of the needle distal portions 81 to the hand-side operating unit 70. The terminal on the proximal side of the needle proximal portion 82 is interlocked with a needle operating lever 78 which is provided in the hand-side operating unit 70 for operating the needle portion 80.

Figure 10:
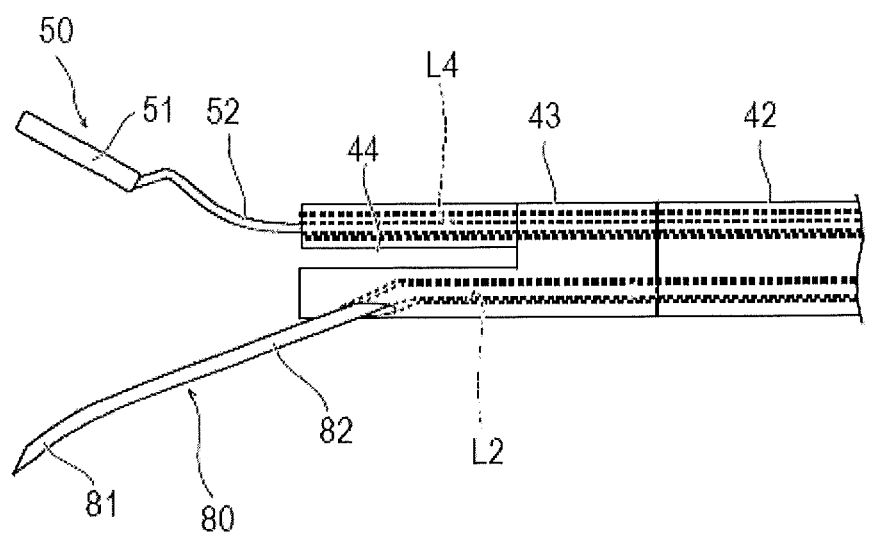
FIG. 10 is a plan view of the distal portion of the catheter which shows a state when a sandwich portion and a needle portion protrude from a lumen.
Figure 11:
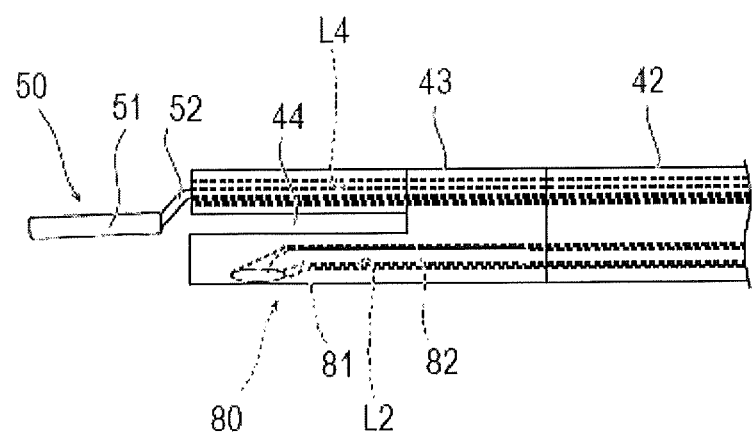
FIG. 11 is a plan view of the distal portion of the catheter which shows a state when the sandwich portion and the needle portion are stored in the lumen.

The needle distal portions 81 are held by (positioned in) two lumens L1 and L2 (refer to FIG. 9) which are formed in the catheter main body 42 and the distal end tip 43 so that the needle distal portions 81 are movable forward and backward, and sharp distal portions of the needle distal portions are configured so as to be retractable from the distal end tip 43 by moving the needle distal portions 81 forward and backward in an axial direction as shown in FIGS. 10 and 11.

Both the sandwich portion 50 and the needle portion 80 function as electrodes for applying an electric current to a biological tissue M. The wire portion 52 of the sandwich portion 50 or the needle portion 80 is inserted into the catheter main body 42 and is electrically connected to the energy supply means 4 for supplying electrical energy through an input connector 75 which is provided in the hand-side operating unit 70, an output connector 87 (refer to FIG. 7) which is a plug fitted into the input connector, a conductive wire d (a generic identifier for d1 and d2) which is connected to an electrode terminal of the output connector 87, and a control portion 5. In addition, either one of the conductive wires d1 and d2 (conductive wire d1 in the present embodiment) is provided with a foot switch SW, to be installed at the feet of an operator in order to control turning-on and turning-off of the electric current from the energy supply means 4. Note that a switch which can be easily operated on the hand side may also be used instead of the foot switch SW.

The hand-side operating unit 70 is a unit for operating the clamping means K, formed of a pair of electrode members which sandwich the biological tissue M lying in the vicinity of a defect existing in the biological tissue, such that the clamping means is retractable backward from the distal end of the catheter main body 42. Means and the like described below are collectively provided in the hand-side operating unit such that all operations can be performed within a small area without significant movement of the hand of an operator.

That is, the hand-side operating unit 70 is provided with, as shown in FIGS. 7 and 8, a main body portion 71 which is on a side on which the guiding sheath 3 is interlocked; a slide portion 100 which operates the positioning and holding means 60; a needle operating lever 78 which operates the needle portion 80 which is one electrode member; a sandwich portion-operating lever 72 which operates the sandwich portion 50 which is the other electrode member; and an operation wire 45 which is inserted into the hand-side operating unit 70 and the catheter main body 42 so as to be movable in the axial direction and which assists the operation of the clamping means K. The hand-side operating unit 70 is further provided with a grasping member 46 which is interlocked with the proximal portion of the operation wire 45 for operating the operation wire 45; a pusher piece 109 which locks the movement of the operation wire 45 in the axial direction; and the input connector 75 which has an electrode terminal which is connected to the energy supply means 4 for applying thermal energy.

The needle operating lever 78 is provided so as to be slidable on the surface side (upper surface side) of the main body portion 71 and is connected to the proximal side of the needle proximal portion 82 in the main body portion 71. Accordingly, when the needle operating lever 78 is made to slide on the surface of the main body portion 71, the needle portion 80 is moved forward and backward.

In addition, the sandwich portion-operating lever 72 is also provided so as to be slidable on the surface side (upper surface side) of the main body portion 71 and is connected to the wire portion 52 of the sandwich portion 50 in the main body portion 71. Accordingly, when the sandwich portion-operating lever 72 is made to slide on the surface of the main body portion 71, the sandwich portion 50 is moved forward and backward.

Figure 15A:
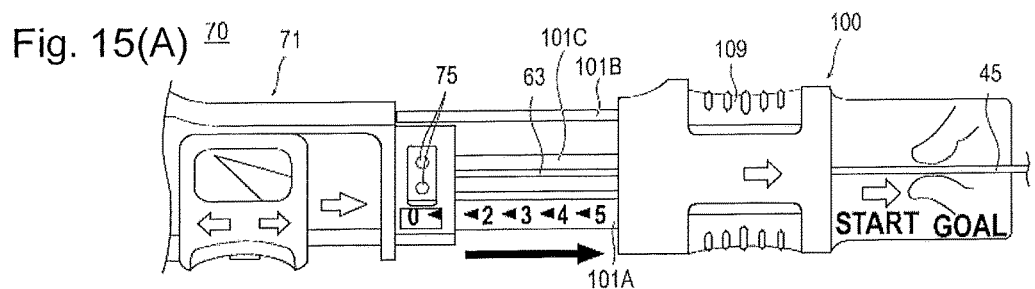
Figure 15B:
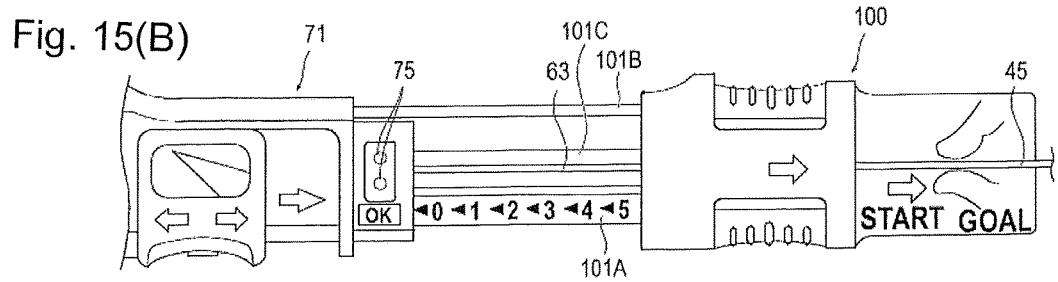

As shown in FIG. 15, the slide portion 100 is interlocked with the proximal side of the main body portion 71 through guide bars 101A, 101B, and 101C for movement toward and away from the main body portion 71. The guide bars 101A, 101B, and 101C are provided so as to be slidable in the main body portion 71.

A main tube 63, to be described in detail later, is inserted into (positioned in) the internal space of the main body portion 71. The proximal side of the main tube 63 is interlocked with the slide portion 100 using an adhesive or the like (refer to FIG. 13) and slides by being guided to the main body portion 71 in accordance with the slide operation of the slide portion 100.

The operation wire 45 is provided inside the main tube 63 and has a function of assisting the operation of the clamping means K by being subjected to a pulling operation in the axial direction, and it is configured so as to be rotatable by 360 degrees around the axial line (central axis), in the main tube 63.

Figure 12:
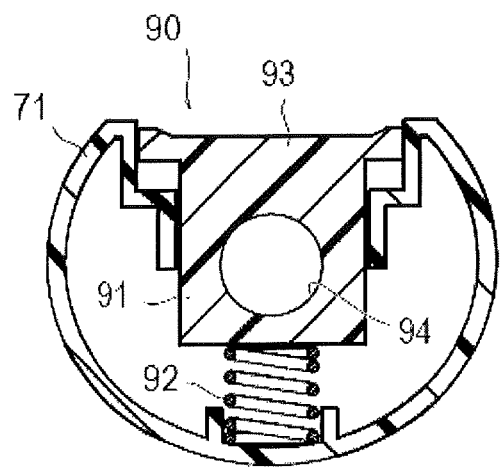
FIG. 12 is a cross-sectional view showing an interlock mechanism taken along line 12-12 in FIG. 8.

As shown in FIGS. 8 and 12, a push button 93 for an interlock mechanism 90 is provided at the distal portion of the main body portion 71. The interlock mechanism 90 is a mechanism for simplifying detachment and attachment of the guiding sheath 3 with respect to the main body portion 71. When the pressing force to the push button 93 is released after a flange portion which is provided at the proximal portion of the guiding sheath 3 is fitted into an insertion hole formed in the main body portion 71 while pushing the press button 93, the flange portion of the guiding sheath 3 engages with the main body portion 71. The interlock mechanism is configured such that the guiding sheath 3 is detachable due to further pressing the press button 93, which is elastically urged by the spring member, and fulfills the locking function of the flange portion. A side port 3A is formed on the proximal side of the guiding sheath 3 and a contrast agent or the like can be injected through the side port 3A.

As shown in FIG. 8, an electrode terminal of the input connector 75 is disposed at the proximal portion of the main body portion 71.

Figure 13:
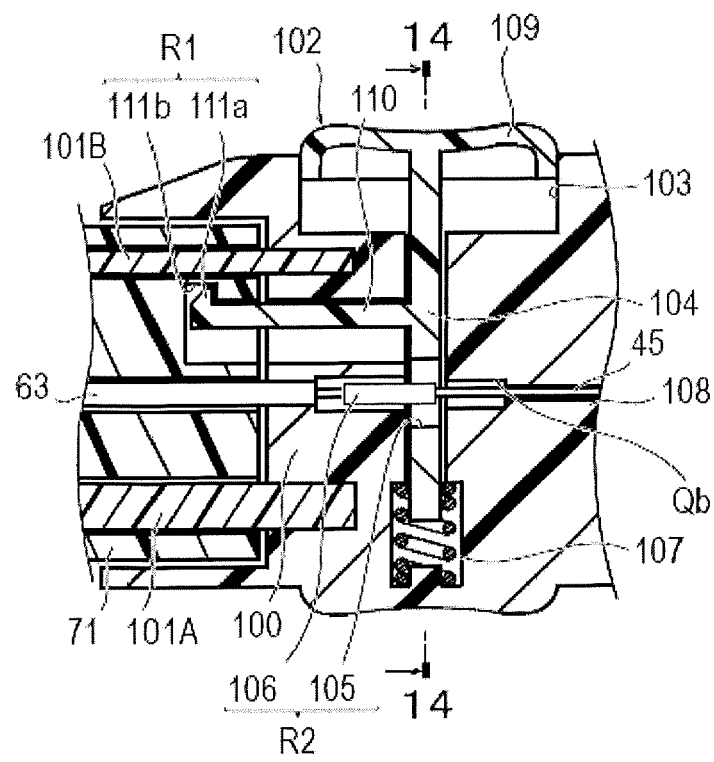
FIG. 13 is a cross-sectional view of a portion of a lock/unlock mechanism taken along line 13-13 in FIG. 8.
Figure 14:
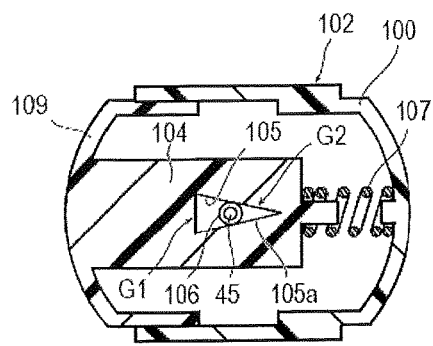
FIG. 14 is a cross-sectional view taken along the section line 14-14 of FIG. 13.

A lock/unlock mechanism 102 shown in FIGS. 13 and 14 is provided in the slide portion 100. By pressing the pusher piece 109, the lock/unlock mechanism locks and unlocks the slide movement of the slide portion 100 and the movement of the operation wire 45 in the axial direction.

The lock/unlock mechanism 102 includes a first lock portion R1 for a slide portion, which interlocks the slide portion 100 and the main body portion 71 by sliding an operation member 104 or makes the slide movement possible by releasing the lock; and a second lock portion R2 for an operation wire which temporarily stops the forward/backward operation of the operation wire 45 in the axial line direction when the positioning and holding means 60, to be described later, which is provided at the distal portion of the operation wire 45 holds or positions the biological tissue M.

The first lock portion R1 includes the operation member 104 that is freely slidable in a slide hole 103 which is formed at the slide portion 100; and a restricting rod 110 which is integrally provided with the operation member 104 and restricts the movement of the slide portion 100 with respect to the main body portion 71. The reference numeral "107" in FIGS. 13 and 14 indicates a spring.

An engagement protrusion 111a which is engaged with an engagement concave portion 111b of the main body portion 71 is provided at the distal end of the restricting rod 110. Therefore, when the operation member 104 is pressed, the engagement between the engagement protrusion 111a and the engagement concave portion 111b is released, thereby enabling the slide portion 100 to slide with respect to the main body portion 71. In addition, the second lock portion R2 is also provided in the operation member 104 and released by the pressure of the operation member 104.

By linking the release of the first lock portion R1 and the release of the second lock portion R2 through the operation of the pusher piece 109 and the operation member 104 in this manner, it is possible to link the operation of pulling out the long (elongated) operation wire 45 from the left atrium L side and the operation of making the operation wire 45 be in a linear shape in order to pull out the operation wire 45. Therefore, it is possible to prevent the pulling operation in a state where the operation wire 45 is curved, which may possibly cause damage to the biological tissue M, in advance or to prevent a situation where the biological tissue M is damaged or fractured in advance.

In contrast, the second lock portion R2 for the operation wire 45 is constituted of a latch section 105 which is formed in the operation member 104; and a large diameter portion 106 which has an outer diameter larger than that of the operation wire 45 and is fixed to the operation wire 45. Examples of the material forming the large diameter portion 106 include stainless steel (stainless steel pipe) or the like. The large diameter portion 106 is fixed to the operation wire 45 using a well-known technique such as welding, adhering, fusing, or the like depending on the material. In the second lock portion R2, the latch section 105 which is provided in the operation member 104 is formed as a wedge-shaped through-hole having a wide width portion G1 and a narrow width portion G2 shown in FIG. 14 in order to temporarily stop the forward/backward operation of the operation wire 45 in the axial line direction. By employing such a wedge-shaped through-hole, the sandwiching of the large diameter portion 106 becomes stronger by simply moving the operation wire 45 within the through-hole.

When performing the surgical procedure using the closing device 40, a puncturing (or piercing) operation using the needle portion 80 is performed after the positioning and holding means 60 performs the holding or positioning of the biological tissue M, and the holding or the positioning of the biological tissue M is performed by pulling out the operation wire 45. Even if the holding or the positioning of the biological tissue M is performed by pulling out the operation wire 45, it is impossible to perform the puncturing operation if the holding state or the positioning state is not maintained. Accordingly, even if the second lock portion R2 latches the large diameter portion 106 with the latch section 105 (rim portion 105a of a through-hole depending on the situation) when pulling out the operation wire 45, the operation wire 45 is temporarily brought into a locked state, and the hand of an operator which grasps the operation wire 45 is then released, it is possible to maintain the holding state or the positioning state and to independently perform only the puncturing operation using the needle portion 80.

In addition, if the lock is released, the shape of the distal portion of the operation wire 45 automatically becomes straight by the elasticity of linear portions 66 and 67 in the holding portion 62, to be described later, and the holding state of the foramen ovale valve M2 can be simply released.

A movement restriction hole 108 which has a size which the large diameter portion 106 cannot pass through in the proximal direction is formed in the internal path into which the operation wire 45 of the slide portion 100 is inserted. Accordingly, it is possible to pull out the operation wire 45 until the large diameter portion 106 which is fixed to the operation wire 45 reaches the movement restriction hole 108. However, the operation wire 45 cannot be further moved to the slide portion 100.

The energy supply means 4 shown in FIG. 7 is used for supplying electrical energy to the clamping means K and a detailed description of the energy supply means 4 will not be repeated since the energy supply means has a well-known system configuration. It is preferable that electrical means is employed regardless of a DC power source or an AC power source in view of ease of control. However, the energy supply means is not limited thereto and any energy supply means may be used as long as it is possible to supply energy by which the foramen ovale valve M2 and the atrial septum M1, which are sandwiched by the clamping means K, can be fused through heating and can be pressed and bonded by an adhesion factor such as collagen, elastin or the like. For example, it is also possible to use ultrasound, lasers, microwaves, high frequency waves, or the like.

As shown in FIG. 8, the positioning and holding means 60 generally includes a needle positioning portion 61 for positioning the needle portion 80 with respect to the foramen ovale O; the holding portion 62 for holding the foramen ovale valve M2 so as not to be movable backward with respect to the puncturing direction of the needle portion 80; and the main tube 63 which is fixedly held by the slide portion 100. The positioning and holding means is usually accommodated in the guiding sheath 3. However, when in use, the positioning and holding means is pressed out from the guiding sheath 3 through the operation of operation wire 45, the main tube 63, and the like as shown in the drawings.

More specifically, the main tube 63 and the operation wire 45 which is provided so as to freely move forward and backward in the main tube 63 in the axial direction are provided in a central lumen L5 which is formed in the distal end tip 43 (refer to FIG. 9). The main tube 63 is a tube of which the proximal side is held fixedly at the slide portion 100 and which exhibits a function as a central axis of the device (i.e., the central axis of the main tube 63 represents the central axis of the overall device). In addition, the main tube also reinforces the catheter main body 42 and draws and withdraws the positioning and holding means 60 into the catheter main body 42. The operation wire 45 passes through the inside of the main tube 63 from the distal end of the catheter main body 42, passes through an internal path of the slide portion 100, and protrudes from the rear end of the slide portion 100. The grasping member 46 for being grasped by the hand of an operator is interlocked with the proximal portion of the operation wire 45 in order to move the operation wire 45 forward and backward, and to rotate the operation wire.

Figure 16A:
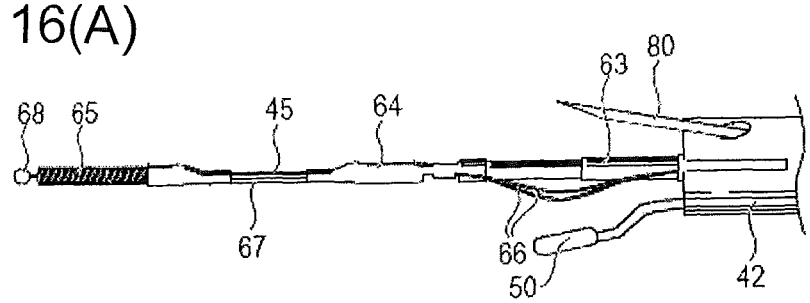
Figure 16B:
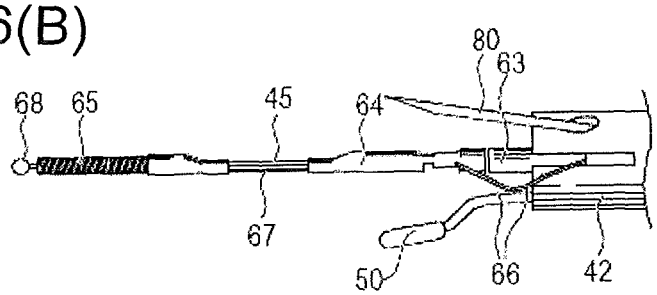

The needle positioning portion 61 is provided at the distal portion of the main tube 63. The needle positioning portion 61 positions the needle portion 80 with respect to the foramen ovale O. The needle positioning portion includes, as shown in FIG. 8, a pair of first linear portions 66 which are elastically expanded and contracted through the operation of the operation wire 45. The proximal ends of the first linear portions 66 are attached to the outer surface of the main tube 63 and the distal ends of the first linear portions 66 are attached to an intermediate cylindrical portion 64 into which the operation wire 45 is inserted. The proximal side of the intermediate cylindrical portion 64 is inserted into the main tube 63 so as to be slidable. As shown in FIGS. 16(A) and 16(B), the needle positioning portion 61 displaces the first linear portions 66 outward by making both ends, which are attached to the main tube 63 and the intermediate cylindrical portion 64, serve as supporting points through the operation of making the operation wire 45 move forward and backward in the axial direction. Each of the first linear portions 66 presses the inner edge of the foramen ovale O with approximately equal elastic force and aligns the needle portion 80 with respect to the foramen ovale O. That is, it is possible to exhibit a function of positioning the needle portion 80 which is positioned between both the first linear portions 66 at a central portion of the foramen ovale O.

The two first linear portions 66 are formed of, for example, a NiTi alloy or the like which is a superelastic material. However, the material forming the two first linear portions 66 is not limited to such material, and for example, stainless steel or the like may be used.

The first linear portions 66 can protrude outward in the diameter direction through the groove portion 44 which is formed in the distal end tip 43. In this manner, it is possible to locate the position in the rotating direction of the main tube 63, with which the first linear portions 66 are interlocked, at a predetermined position with respect to the catheter main body 42 which is provided with the distal end tip 43, by making at least the proximal sides of the first linear portions 66 coincide with the groove portion 44.

In contrast, the holding portion 62 is a portion which holds the needle portion 80 from the rear surface side so as to easily puncture the foramen ovale valve M2 and includes a distal member 68, which is provided at the distal portion of the operation wire 45; a distal end cylindrical portion 65 into which the operation wire 45 is inserted; a pair of second linear portions 67 which is integrally formed with the distal end cylindrical portion 65; and a reinforcing member 69 for reinforcing the distal end cylindrical portion 65 by being fixed to the proximal side of the distal end cylindrical portion 65.

The distal member 68 is fixed to the distal end of the operation wire 45, the operation wire 45 is inserted into the distal end cylindrical portion 65 and the intermediate cylindrical portion 64, the proximal ends of the second linear portions 67 are fixed to the distal end of the intermediate cylindrical portion 64, and the distal sides of the second linear portions 67 are fixed to the distal end cylindrical portion 65. The intermediate cylindrical portion 64 and the reinforcing member 69 are formed by, for example, processing a metal tube made of stainless steel or the like.

The intermediate cylindrical portion 64, the distal end cylindrical portion 65, the second linear portions 67 which interlock both the cylindrical portions 64 and 65, the distal member 68, and the reinforcing member 69 constitute a curving mechanism W which bends or curves the distal portion of the operation wire 45.

Figure 16C:
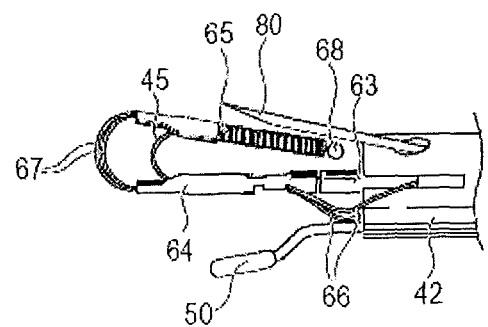

The curving mechanism W is used for holding the foramen ovale valve M2. When the foramen ovale valve M2 is punctured with the needle portion 80, the puncturing is easier if the thin foramen ovale valve M2 is held from the rear surface side of the foramen ovale valve M2. Accordingly, the curving mechanism W is configured such that the second linear portions 67 are bent or curved between the distal member 68 and the distal sides of the first linear portions 66 as shown in FIGS. 16(B) and 16(C) by moving the operation wire 45 backward in the axial direction and the foramen ovale valve M2 is held by the distal member 68 and the distal end cylindrical portion 65 from the rear surface side. That is, the curving mechanism W is configured such that the distal portion of the operation wire 45 is bent or curved by making the distal sides of the first linear portions 66, which are attached to the main tube 63, serve as supporting points.

However, it is necessary for the curving mechanism W of the holding portion 62 to be configured so as to be curved and hold the foramen ovale valve M2 after the first linear portions 66 of the needle positioning portion 61 align and position the needle portion 80 with respect to the foramen ovale O. Thus, it is necessary for the first linear portions 66 to deform prior to the second linear portions 67. Therefore, in the present embodiment, the elastic members are made with different rigidity from each other.

When the slide portion 100 is moved forward and backward with respect to the main body portion 71, it is possible for the main tube 63 fixed firmly to the slide portion 100 to be drawn into the lumen L5 in the center of the catheter main body 42 and along with this operation, it is possible to withdraw the entire positioning and holding means 60 into the catheter main body 42.

Next, an operation of the medical device according to the first embodiment will be described.

(1) Preceding Process

Figure 17:
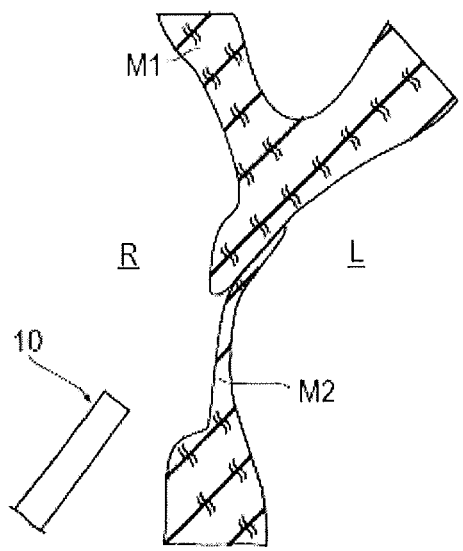
FIG. 17 is a schematic cross-sectional view showing a state when the long sheath is made to reach the right atrium.

An operator inserts an introducer (assembly in which a dilator is inserted into the long (elongated) sheath 10) through the femoral vein. After the distal end of the long sheath 10 reaches the right atrium R through the inferior vena cava J, the dilator is removed from the long sheath 10. Accordingly, the device enters or is in a state where the distal portion of the long sheath 10 is held in the right atrium R as shown in FIG. 17. Note that the region into which the long sheath 10 is to be inserted is not limited to the femoral vein, and for example, the axillary vein, the subclavian vein, the internal jugular vein and the like may be selected.

(2) Expansion Process Using Long Instrument

Figure 18:
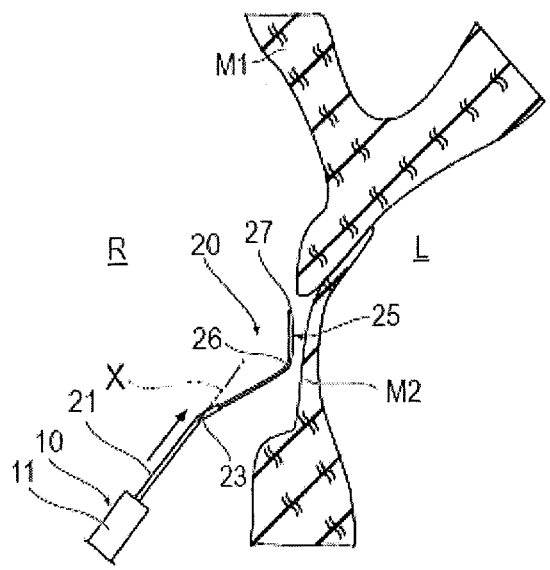
FIG. 18 is a schematic cross-sectional view showing a state when the long instrument is made to reach the right atrium.

Next, the operator inserts the long instrument 20 into the sheath portion 11 of the long sheath 10 through the valve body 13 which is provided in the hub portion 12 of the long sheath 10. Accordingly, the shaft bent portion 23 and the pressing portion 26, which are normally bent in the absence of any applied force or load, deform so as to extend in a linear shape, and the shaft portion 21 and the distal end deformation portion 25 are accommodated in the sheath portion 11 by being in a substantially linear shape (refer to FIG. 5(A)). Then, when the operator presses or moves the shaft portion 21 along the long sheath 10, the distal end deformation portion 25 of the long instrument 20 is exposed in the right atrium R by protruding from the opening portion on the distal side of the long sheath 10 (i.e., the distal end deformation portion 25 extends distally beyond the open distal end of the long sheath 10). Then, as shown in FIG. 18, two pressing portions 26 are expanded in the expansion direction A intersecting or transverse to the shaft center (central axis of the shaft) X direction of the shaft portion 21 and the shape of the shaft bent portion 23 returns to its bent shape, and therefore, is restored to its original shape using its self-restoring force (expansion process).

(3) Separation Process

Figure 19:
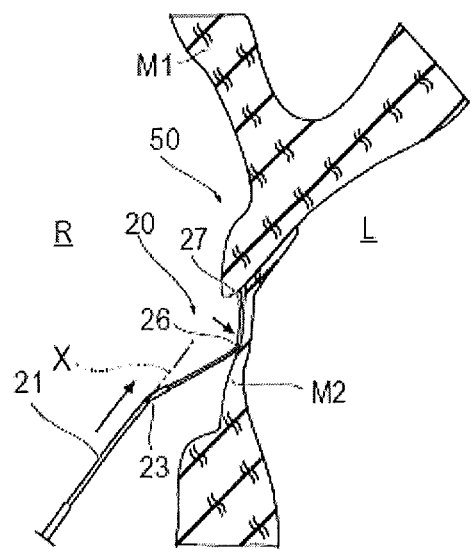
FIG. 19 is a schematic cross-sectional view showing a state when the long instrument is thrust between the atrial septum and the foramen ovale valve.

Next, as shown in FIG. 19, the two pressing portions 26 are positioned to abut on the foramen ovale valve M2, and the thrusting portion 27 is thrust or moved forwardly into the joint portion between the atrial septum M1 and the foramen ovale valve M2 while pressing the foramen ovale valve M2 to the left atrium L side using the pressing portions 26. At this time, the shaft portion 21 hardly comes into contact with the foramen ovale valve M2 due to the provision of the shaft bent portion 23, which is formed so as to be bent in the direction away from the shaft center (central axis of the shaft) X of the shaft portion 21, on the proximal side of the pressing portions 26 which are positioned away from the shaft center X of the shaft portion 21, and therefore, it is possible to effectively press the foramen ovale valve M2 to the left atrium L side, that is, in a direction away from the atrial septum M1.

Figure 20:
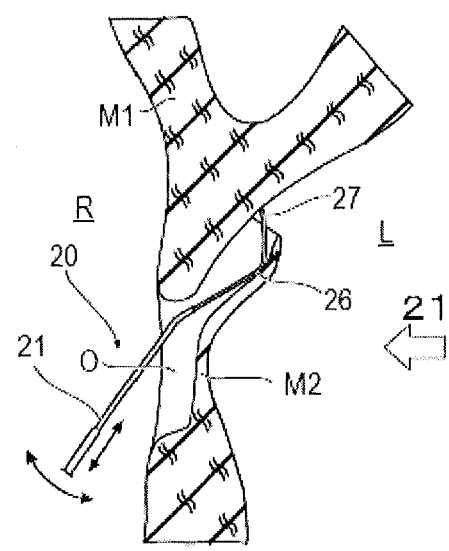
FIG. 20 is a schematic cross-sectional view showing a state when a foramen ovale is formed using the long instrument.
Figure 21:
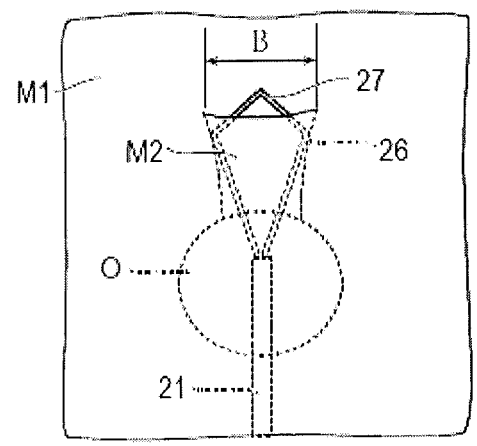
FIG. 21 is a schematic view showing the heart septum and the foramen ovale valve when viewed from the arrow 21 in FIG. 20.

In addition, since the pressing portions 26 are bent, the thrusting portion 27 which is further on the distal side than the pressing portions 26 is positioned in a direction different from the direction in which the pressing portions 26 are positioned, with respect to the shaft portion 21. For this reason, when pressing the foramen ovale valve M2 to the left atrium L side using the pressing portions 26, it is rather easy to position the thrusting portion 27 further on the right atrium R side than the pressing portions 26, and therefore, it is possible to effectively thrust the thrusting portion 27 into the joint portion between the atrial septum M1 and the foramen ovale valve M2. Then, the thrusting portion 27 is thrust into the joint portion between the atrial septum M1 and the foramen ovale valve M2 on which tensile force is exerted in a direction away from each other while moving the foramen ovale valve M2 in a direction away from the atrial septum M1 by pressing the foramen ovale valve using the pressing portions 26 while applying a forward/backward movement, a rotary movement, or the like to the shaft portion 21 depending on the situation. By doing this, as shown in FIGS. 20 and 21, the foramen ovale valve M2 is effectively separated from the atrial septum M1 and a foramen ovale O is formed which is configured such that the foramen ovale valve M2 overlaps the atrial septum M1. At this time, it is possible to exert a larger force on either of the pressing portions 26 or the thrusting portion 27 by making the other side serve as a supporting point or fulcrum, using the principle of a lever. In this manner, it is possible to form the foramen ovale O on the biological tissue M without puncturing the biological tissue M and while reducing the influence on a living body.

In addition, since the thrusting portion 27 is positioned substantially on an extension line of the shaft center (central axis of the shaft) X of the shaft portion 21, when the shaft portion 21 is moved forward along the shaft center X, the shaft portion 21 receives force from the extension line of the shaft center X. Therefore, it is difficult to cause a phenomenon in which force escapes due to the bending of the shaft portion 21. For this reason, it is possible to effectively transmit action force generated by the forward/backward movement of the shaft portion 21 to the thrusting portion 27 and to effectively separate the foramen ovale valve M2 from the atrial septum M1.

In addition, the two pressing portions 26 have a predetermined width in an expanded state, and therefore, it is possible to form a foramen ovale O with a desired width B. In addition, since the distal end deformation portion 25 is formed so as to have a width which becomes narrower toward the thrusting portion 27 from the pressing portions 26, the foramen ovale O becomes larger as the distal end deformation portion is pressed to the deep portion of the joint portion. Therefore, the size of the foramen ovale O can be adjusted with one instrument, thereby reducing the cost. The width B of the foramen ovale O to be formed can be appropriately set depending on the outer diameter of the treatment instrument 30 or the like, and examples thereof include 5 mm to 20 mm. However, the present invention is not limited to these examples of widths.

(4) Process of Inserting Long Sheath

Figure 22:
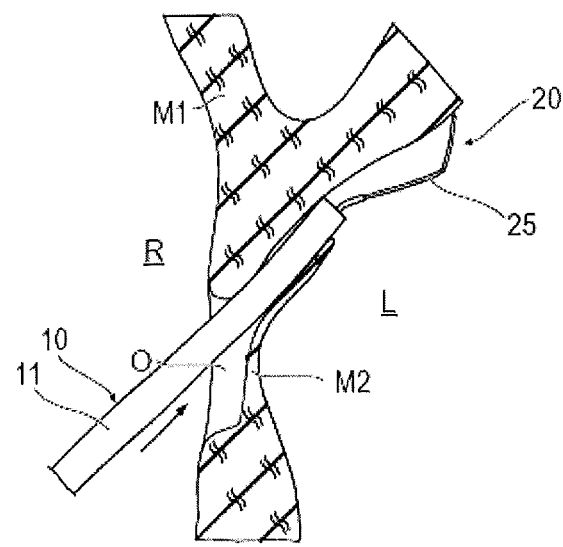
FIG. 22 is a schematic cross-sectional view showing a state when the long sheath is made to reach the left atrium through the foramen ovale.
Figure 23:
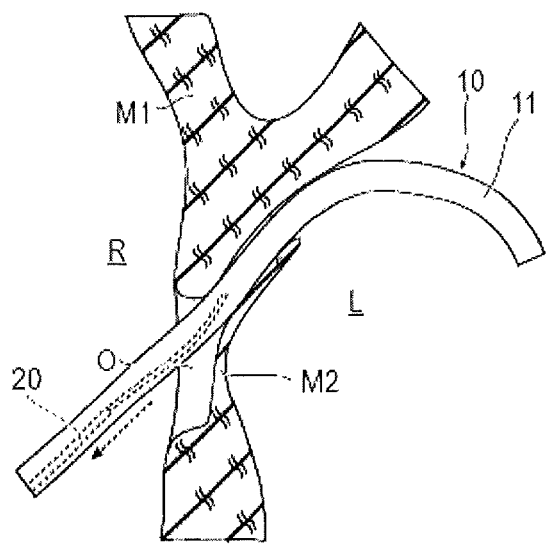
FIG. 23 is a schematic cross-sectional view showing a state when the long instrument is pulled out from the long sheath.

After the foramen ovale O is formed by the long instrument 20, as shown in FIG. 22, the long sheath 10 is pressed or moved forward while using the long instrument 20 as a guide in a state where the distal end deformation portion 25 of the long instrument 20 is positioned in the left atrium L, and the distal portion of the long sheath 10 is inserted into the foramen ovale O and reaches the left atrium L side. Accordingly, a path for accessing the left atrium L side from the right atrium R side is secured in the long sheath 10. Then, the long instrument 20 is pulled out from the long sheath 10 while leaving the long sheath 10 as shown in FIG. 23. At this time, the distal end deformation portion 25 is pulled out from the valve body 13 of the hub portion 12 through the inside of the sheath portion 11 by being in a substantially linear shape.

(5) Treatment Process

Figure 24:
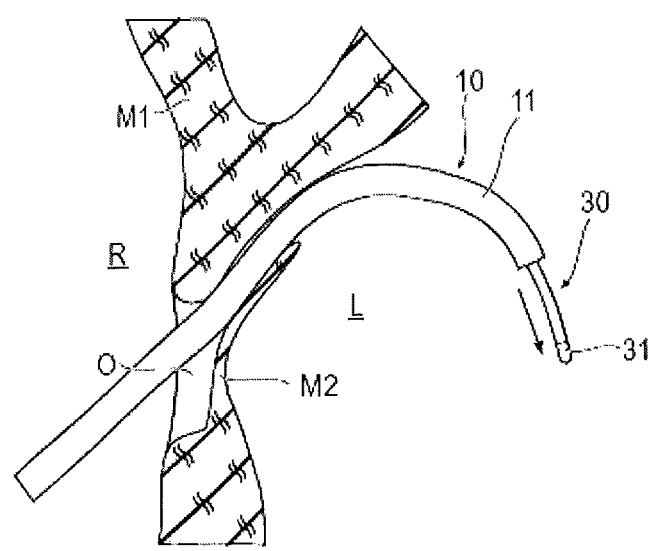
FIG. 24 is a schematic cross-sectional view showing a state when an ablation catheter is made to reach the left atrium through the long sheath.

Next, an ablation catheter as the treatment instrument 30 is inserted into the sheath portion 11 through the valve body 13 which is provided in the hub portion 12 of the long sheath 10. Since the long sheath 10 is inserted into the left atrium L, it is possible for the ablation catheter to rather easily reach the left atrium L as shown in FIG. 24. Then, a joint portion between the left atrium L and the pulmonary vein is ablated by the ablation catheter to complete the treatment. Thereafter, the ablation catheter is pulled out from the long sheath 10.

(6) Preceding Process of Closing Foramen Ovale

Thereafter, the pusher piece 109 of the first lock portion R1 in the lock/unlock mechanism 102 of the closing device 40 is pressed inward of the slide portion 100, the operation member 104 is lowered inside the slide hole 103, and the restriction of the restricting rod 110 is released, before closing of the foramen ovale O is performed using the closing device 40 (refer to FIG. 13). Accordingly, the slide portion 100 enters or is in a movable state with respect to the main portion 71. Next, the main tube 63, the wire portion 52 of the sandwich portion 50, the needle portion 80, and the like are accommodated in the catheter main body 42 by moving the slide portion 100 backward with respect to the main body portion 71 and also moving the needle operating lever 78 and the sandwich portion-operating lever 72 backward.

Figure 25:
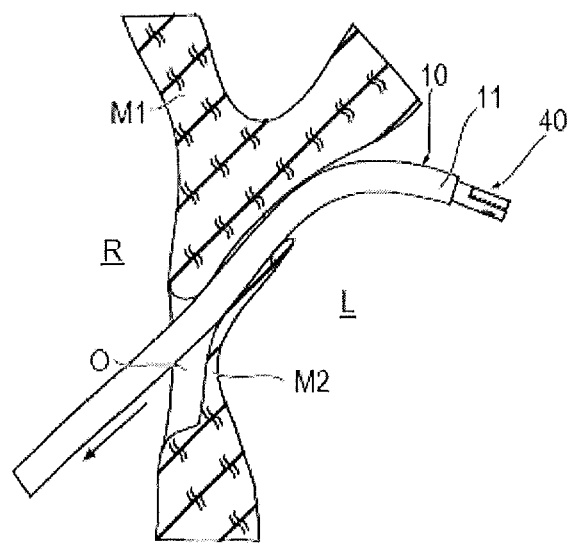
FIG. 25 is a schematic cross-sectional view showing a state when the closing device is inserted into the left atrium through the long sheath.

In this state, the catheter main body 42 is inserted into the long sheath 10 together with the guiding sheath 3 and is made (forwardly moved) to reach the left atrium L through the inferior vena cava J and the right atrium R as shown in FIG. 25. When the distal end of the catheter 41 reaches the left atrium L, the long sheath 10 is moved backward and the distal portion of the long sheath 10 is pulled back to the right atrium R. Then, the slide portion 100 is moved forward with respect to the main body portion 71. Accordingly, the pusher piece 109 of the lock/unlock mechanism 102 is pressed along with the forward movement of the main tube 63 (refer to FIG. 14). Thus, a state is brought about in which the large diameter portion 106 of the operation wire 45 does not abut on the narrow width portion G2 of the through hole 105 which is formed in the operation member 104, in other words, the second lock portion R2 enters or is in an unlocked state and the operation wire 45 enters or is in a free state (freely movable state).

Then, the positioning and holding means 60 moves forward due to the main tube 63 which is fixed to the slide portion 100 and the sandwich portion 50 also moves forward by moving the slide portion 100 forward with respect to the main body portion 71.

When the slide portion 100 is moved by a predetermined length, the movement of the sandwich portion 50 becomes independent of the slide portion 100 due to a switching mechanism (not shown) in the main body portion 71, and therefore, it is possible to operate only the sandwich portion 50 using the sandwich portion-operating lever 72 without affecting the main tube 63 which moves in conjunction with the slide portion 100.

Figure 26:
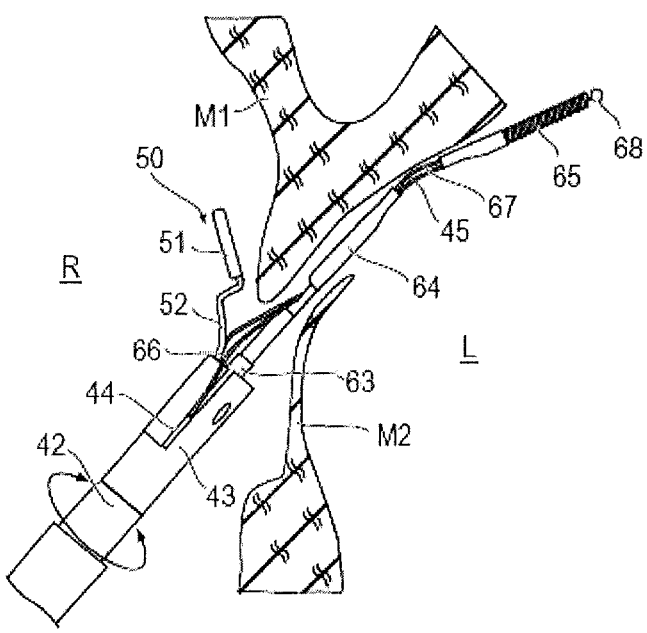
FIG. 26 is a schematic cross-sectional view showing a state when the positioning and holding means is inserted into the foramen ovale.

Then, the hand-side operating unit 70 is pulled out in a state where the operation wire 45 is inserted into the left atrium L, until the opening portions of the lumens L1 to L5 reach the right atrium R as shown in FIG. 26. At this time, the distal end of the operation wire 45 protrudes from the distal end cylindrical portion 65 and is positioned in the left atrium L. Then, since the wire portion 52 enters or is in a state of protruding from the lumens L3 and L4, the flat plate portion 51 is in or enters a state of being separated from the atrial septum M1.

Note that the closing device 40 may be inserted into the left atrium L side from the right atrium R side by making the closing device 40 reach the right atrium R side using the long sheath 10 after moving the long sheath 10 backward to the right atrium R side, without making the closing device 40 reach the left atrium L side using the long sheath 10. In this case, first, the distal end of the operation wire 45 is made to protrude from the distal end cylindrical portion 65, from the distal end of the main tube 63. This protruding state can be visually checked from outside since an X-ray impermeable marker is provided in the distal member 68. The operation wire 45 is rotatable by 360 degrees, and therefore, it is possible to move the operation wire 45 forward while rotating the operation wire and to easily insert the operation wire into the left atrium L.

In addition, it is possible to insert the catheter main body 42 into the right atrium R or the left atrium L using the long sheath 10 instead of the guiding sheath 3, without using the guiding sheath 3.

(7) Process of Pulling Out Operation Wire

In the pulling process, the operator confirms the position of the distal end of the operation wire 45, and then, the operation wire 45 is moved backward by pulling the grasping member 46 until the distal member 68 at the distal end of the operation wire 45 abuts on the distal end cylindrical portion 65 as shown in FIG. 16(A).

When the operation wire 45 is moved backward, the large diameter portion 106 also moves backward. In the lock/unlock mechanism 102, the operation member 104 is biased upward by the resilient force of the spring 107 unless the pusher piece 109 is pressed. Accordingly, the operation wire 45 is pressed and held between the narrow width portion G2 of the wedge-shaped through-hole 105 and the inner circumferential surface of an internal path Qb by force with which the operation wire can slide at all times. Therefore, it is possible to carry out the pulling operation relatively smoothly with respect to the backward movement of the operation wire 45. Then, the main body portion 71 is operated and the second linear portions 67, the sandwich portion 50, and the needle portion 80 are positioned near the foramen ovale valve M2, and the entire holding portion 62 enters or is in a state of being inserted to the left atrium L side.

When the operation wire 45 is moved further backward, this operating force for causing backward movement is transmitted to a first linear portion 66, of which the proximal end is attached to the main tube 63, by the operation wire 45 through the distal member 68, the distal end cylindrical portion 65, the second linear portion 67, and the intermediate cylindrical portion 64. The first linear portion 66 deforms, in a protruding manner, into an arc shape outward in the diametrical direction as shown in FIGS. 16(B) and 26. At this time, a part of the proximal side of the first linear portion 66 is fitted into the groove portion 44 of the distal end tip 43. Accordingly, the rotating direction of the main tube 63 with which the first linear portion 66 is interlocked is positioned at an appropriate position with respect to the catheter main body 42. However, the second linear portion 67 does not deform at this point in time.

As a result, the first linear portion 66 deforms while pressing and expanding the rim portion of the foramen ovale O, and therefore, the needle portion 80 which is provided in the immediate vicinity of the first linear portion 66 is aligned with respect to the foramen ovale O and the needle portion 80 is positioned at the center of the foramen ovale O.

When the operation wire 45 is further operated so as to move backward and the intermediate cylindrical portion 64 abuts the distal end of the main tube 63 as shown in FIG. 16(C), the first linear portion 66 does not deform much since the intermediate cylindrical portion 64 is suppressed from being further moved backward. Moreover, the second linear portion 67 on the distal side deforms in a protruding manner in an arc shape outward in the diametrical direction due to the operating force and the distal end cylindrical portion 65 and the distal member 68 further on the distal side than the second linear portion 67 move to the extent that they come into contact with the intermediate cylindrical portion 64 while making an arc by being inclined outward in the diameter direction so as to approach the needle portion 80.

Figure 27:
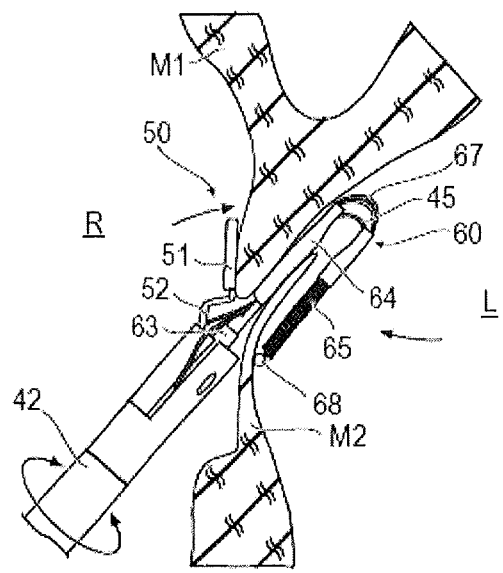
FIG. 27 is a schematic cross-sectional view when the foramen ovale valve and the atrial septum are held by the positioning and holding means.

As a result, as shown in FIG. 27, the distal member 68 and the distal end cylindrical portion 65 move so as to approach the needle portion 80 in the left atrium L, and therefore, abut on the surface on the left atrium L side of the foramen ovale valve M2 so as to hold the foramen ovale valve.

Next, in the second lock portion R2 in the lock/unlock mechanism 102 shown in FIGS. 13 and 14, the large diameter portion 106 is pressed into the latch section 105 which is a wedge-shaped through-hole and the operation wire 45 is locked so that position of the operation wire 45 is fixed. As a result, even if the operator releases a hand from the grasping member 46, the holding state is reliably maintained and the holding of the foramen ovale valve M2 is not loosened. Therefore, the operator can move the needle operating lever 78 using a single hand.

(8) Temporary Grasping Process

In the temporary grasping process, the sandwich portion-operating lever 72 is operated so as to slightly draw the wire portion 52 into the lumens L3 and L4 from a state of protruding from the lumens L3 and L4.

With the operation of the wire portion 52 so as to slightly draw the wire portion into the lumens L3 and L4, the bending of the wire portion 52 extends in the lumens L3 and L4, and elastically deforms into a nearly linear shape, and the flat plate portion 51 is pressed to the atrial septum M1. Due to this operation, the atrial septum M1 is sandwiched between the flat plate portion 51 and the intermediate cylindrical portion 64. Then, in the process of sandwiching the atrial septum M1 between the flat plate portion 51 and the intermediate cylindrical portion 64, the position of the rotating direction of the catheter main body 42 which easily rotates around the axis is corrected and is positioned at a proper rotating direction position with respect to the atrial septum M1. Accordingly, puncturing or heating of the biological tissue M which is to be performed after this can be performed at an intended proper position.

(9) Puncturing Process

Figure 28:
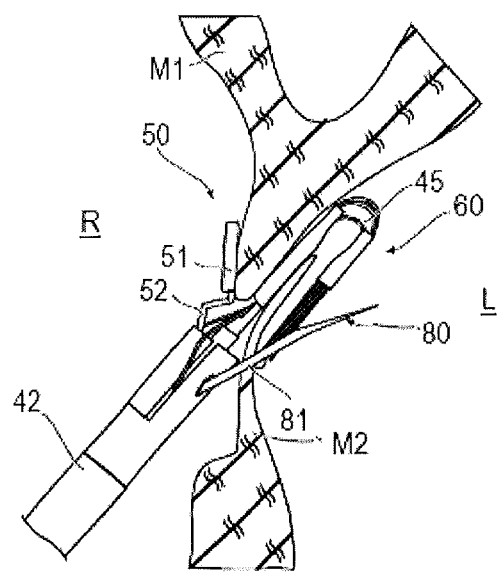
FIG. 28 is a schematic cross-sectional view when the foramen ovale valve is punctured with the needle portion while the foramen ovale valve and the atrial septum are being held.

Next, when the needle operating lever 78 which is provided in the main body portion 71 is moved forward, as shown in FIG. 28, the needle distal portion 81 of the needle portion 80 protrudes from the distal end of the catheter main body 42 and the foramen ovale valve M2 is punctured with the needle distal portion 81 at a predetermined position. Then, once the foramen ovale valve is punctured with the needle portion 80, the position of the needle portion 80 becomes a fixed position in relation to the foramen ovale valve M2. Accordingly, the operator can carry out a process after the puncturing operation in an extremely easy manner.

Figure 29:
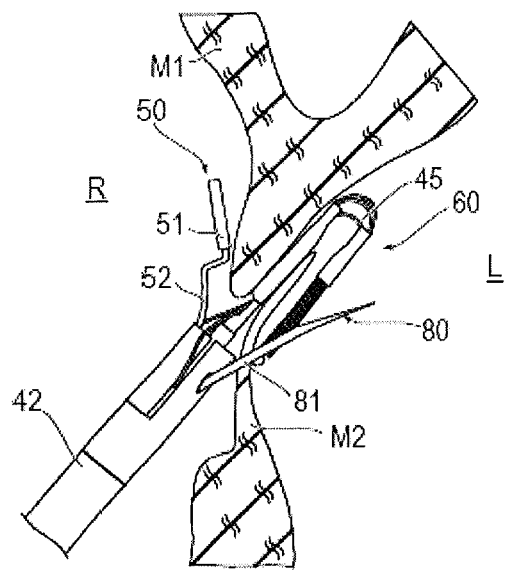
FIG. 29 is a schematic cross-sectional view when the sandwich portion is separated from the atrial septum.

When the puncturing is completed, the sandwich portion-operating lever 72 is operated to make the wire portion 52 protrude from the lumens L3 and L4 to the distal side. Accordingly, the flat plate portion 51 is separated from the atrial septum M1 as shown in FIG. 29.

(10) Process of Moving Slide Portion

Figure 30:
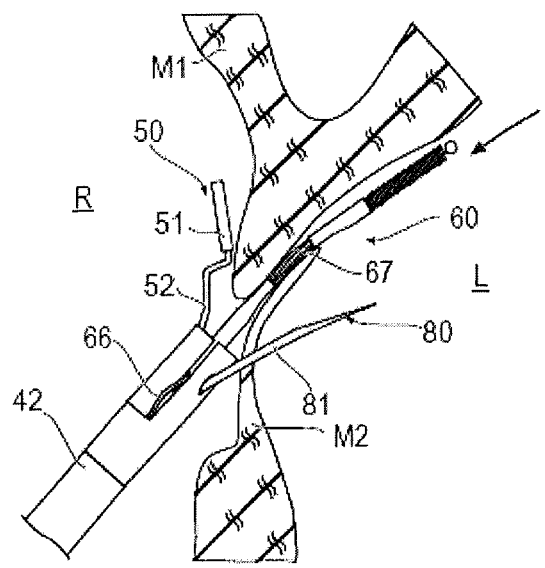
FIG. 30 is a schematic cross-sectional view when the positioning and holding means is accommodated in a main body of the catheter.

Next, if the pusher piece 109 is pressed and the locking of the operation wire 45 is released in order to release the locking of the second lock portion R2 in the lock/unlock mechanism 102 shown in FIGS. 13 and 14, the pressure which is applied to the first linear portion 66 and the second linear portion 67 by the operation wire 45 and the distal member 68 disappears. Then, the first linear portion 66 and the second linear portion 67 enter or move to a linearly extended state due to their own elastic force as shown in FIG. 30. When the slide portion 100 is operated so as to move backward in this state, the entire positioning and holding means 60 is withdrawn into the lumen L5 of the catheter main body 42 through the main tube 63.

(11) Sandwiching Process

Figure 31:
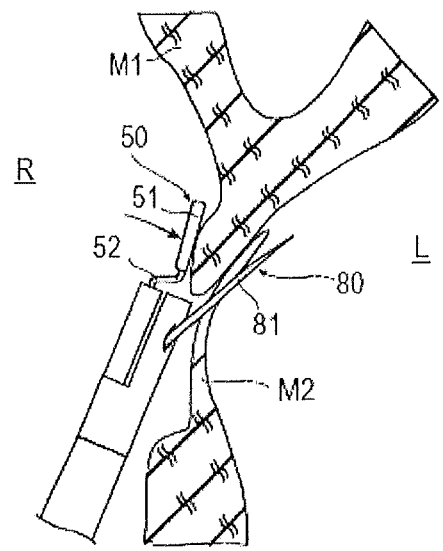
FIG. 31 is a schematic cross-sectional view when the foramen ovale valve and the atrial septum are sandwiched by the needle portion and the sandwich portion.

Then, in the process of moving the slide portion backward, the sandwich portion 50 which has been independent of the slide portion 100 is moved again in conjunction with the switching mechanism (not shown) in the main body portion 71. Accordingly, when the slide portion 100 is moved backward, the flat plate portion 51 moves backward. Then, when the wire portion 52 is drawn into the lumens L3 and L4, as shown in FIG. 31, the flat plate portion 51 abuts on the atrial septum M1 due to the wire portion 52 deforming in a linear shape, and the atrial septum M1 and the foramen ovale valve M2 are sandwiched between the needle distal portion 81 and the flat plate portion 51.

Then, when the output connector 87 is connected to the input connector 75 as shown in FIG. 7, the device enters or is in a state where power supply from the energy supply means 4 is possible. Thereafter, a predetermined amount of electrical energy which is controlled by the control portion 5 is supplied to the sandwich portion 50 and the needle portion 80 by operating the switch SW, and the atrial septum M1 and the foramen ovale valve M2 are heated.

When the heating is continued while maintaining a fusion temperature, the tissues of the atrial septum M1 and the foramen ovale valve M2 are melted and are mutually fused and joined together by adhesive factors such as collagen, elastin, or the like.

(12) Process of Moving Puncturing Portion Backward

When the fusion is completed, the needle operating lever 78 which is provided in the main body portion 71 is moved backward and the needle portion 80 is accommodated in the distal end tip 43. Thereafter, the output connector 87 is removed from the input connector 75.

Then, when the main body portion 71 is moved backward so as to be away from the living body by pressing the push button 93 of the interlock mechanism 90 and releasing the interlock between the guiding sheath 3 and the main body portion 71, the device is pulled out with the guiding sheath 3 as a guide. Thereafter, when the guiding sheath 3 and the long sheath 10 are removed from the living body, the surgical procedure is completed.

As described above, the medical device according to the first embodiment is a medical device for forming a hole (foramen ovale O) by thrusting a thrusting portion 27 into a joint portion of biological tissues M while pressing the biological tissues M using a pressing portion 26, the device including: a shaft portion 21 which is elongated; the pressing portion 26 which is provided on a distal side of the shaft portion 21 and can be expanded and contracted in an expansion direction A intersecting a shaft center X direction of the shaft portion 21; and the thrusting portion 27 which is positioned further on the distal side of the shaft portion 21 than the pressing portion 26 and in a direction which is different from the direction in which the pressing portion 26 is positioned with respect to the shaft portion 21. At least one of the pressing portion 26 and the thrusting portion 27 can be expanded and contracted in the expansion direction A intersecting or transverse to the shaft center X direction of the shaft portion 21. Accordingly, it is possible to contract at least one of the pressing portion 26 and the thrusting portion 27 and to move it to a predetermined place within the body lumen. Moreover, it is possible to efficiently separate the joint portions from one another by thrusting the thrusting portion 27 into the joint portion of the biological tissues M which are positioned in a direction different from a region to be pressed with respect to the shaft portion 21 while pressing the biological tissues M using the pressing portion 26. For this reason, it is possible to form a hole in the biological tissues M without puncturing the biological tissues M and to perform treatment through the formed hole while reducing the influence on the living body.

In addition, when a hole is formed in the atrial septum M1 through a brockenbrough method or the like, it is necessary to confirm the position and the direction to be punctured so as not to puncture the aorta. However, when forming a foramen ovale O through separation as in the present embodiment, there is no concern that the aorta will be punctured, and therefore, the safety and the workability are improved.

In addition, the pressing portion 26 and the thrusting portion 27 are formed of an elastically deformable wire. Therefore, it is possible to rather easily contract and expand the pressing portion 26 and the thrusting portion 27 and to reduce the size of the device due to its relatively simple configuration. Thus, it is possible to reduce the influence on the living body due to the rather easy insertion of the device into the body lumen.

In addition, the pressing portion 26 is positioned away from the shaft center X of the shaft portion 21 when being projected onto a reference surface S which is orthogonal to the expansion direction A of the pressing portion 26 and passes through the shaft center X of the shaft portion 21. That is, the pressing portions are spaced laterally from a plane S which contains the shaft center X, passes through the thrusting portion 27 and is perpendicular to the plane of the paper illustrating FIG. 5(B). Thus, the shaft portion 21 hardly comes into contact with biological tissues M with which the pressing portion 26 comes into contact, and therefore, it is possible to effectively press the biological tissues M using the pressing portion 26.

In addition, the pressing portion 26 comes into contact with the foramen ovale valve M2 on a right atrium R side and presses the foramen ovale valve onto a left atrium L side and the thrusting portion 27 is thrust between the foramen ovale valve M2 and the atrial septum M1, so as to form a foramen ovale O. Thus, the thrusting portion 27 is thrust into the joint portion between the atrial septum M1 and the foramen ovale valve M2 on which tensile force is exerted in a direction away from each other while pressing the foramen ovale valve M2 in a direction away from the atrial septum M1 using the pressing portion 26. Therefore, the foramen ovale O can be rather easily formed which is configured such that the foramen ovale valve M2 overlaps the atrial septum M1 by effectively separating the foramen ovale valve M2 from the atrial septum M1.

Note that the foramen ovale O is usually closed due to the pressure of the left atrium L exceeding the pressure on the right atrium R side. Therefore, influence on a living body is smaller than a case where a hole is formed in the atrial septum M1 through a brockenbrough method or the like, depending on the conditions such as the size of the hole or the like. Thus, it is possible to reduce the risk of cyanosis or cardiac hypertrophy. In addition, the formed foramen ovale O can be closed with the lapse of time.

In addition, the foramen ovale O can be relatively easily formed which allows access between the left atrium L and the right atrium R without puncturing the atrial septum M1 through a treatment method that includes a separation process in which the foramen ovale O is formed by separating the foramen ovale valve M2 and the atrial septum M1 from each other using the long instrument 20 of the medical device which is percutaneously inserted into the right atrium R. Note that in an ordinary heart, the foramen ovale O is closed such that the foramen ovale valve M2 overlaps the atrial septum M1 since the pressure of the left atrium L exceeds the pressure on the right atrium R side. Thus, it is possible to suppress blood flowing into the left atrium L side (artery side) from the right atrium R side (venous side) through the foramen ovale O and thus to reduce the influence on a living body compared to a case in which the atrial septum M1 is punctured.

In addition, the aforesaid treatment method includes a treatment process in which treatment is performed by percutaneously inserting the treatment instrument 30 that performs treatment into the left atrium L from the right atrium R through the foramen ovale O, after the separation process. Therefore, it is possible to perform treatment on the left atrium L side through the foramen ovale O without puncturing the atrial septum M1 and while reducing the influence on a living body.

In addition, the aforesaid treatment method includes a joining process in which the foramen ovale valve M2 and the atrial septum M1 are sandwiched by the needle portion 80 and the sandwich portion 50 which are electrodes, an electric current is made to flow to the needle portion 80 and the sandwich portion 50, and the foramen ovate valve M2 and the atrial septum M1 are joined together, after the treatment process. Therefore, it is possible to occlude the foramen ovale O without attaching an occlusive instrument (such as a disk-like film or an anchor member), which is a foreign material to a living body and can be a factor of forming thrombi, to the foramen ovale. For this reason, in a case where it is necessary to access the left atrium L from the right atrium R again to perform treatment, it is possible to reduce interference on the treatment since no occlusive instrument is attached to the foramen ovale. In addition, it is unnecessary to use the occlusive instrument, and therefore, it is possible to prevent the risk of falling-off of the occlusive instrument.

In addition, the medical device used in the aforementioned treatment method includes the shaft portion 21 which is elongated; the pressing portion 26 which is provided on the distal side of the shaft portion 21 and can be expanded and contracted in the expansion direction A intersecting the shaft center X direction of the shaft portion 21; and the thrusting portion 27 which is positioned further on the distal side of the shaft portion 21 than the pressing portion 26 and in a direction which is different from the direction of the pressing portion 26 with respect to the shaft portion 21. The aforementioned treatment method further includes an expansion process in which the pressing portion 26 is expanded by making the pressing portion 26 protrude from the distal end of the long sheath 10 after positioning the medical device inside of the right atrium R through the inside of the long sheath 10 (tubular body) that is percutaneously inserted into the right atrium R. In the separation process, a foramen ovale O is formed by thrusting the thrusting portion 27 into the joint portion between the foramen ovale valve M2 and the atrial septum M1 while pressing the foramen ovale valve M2 to the left atrium L side using the pressing portion 26. Accordingly, it is possible to move the pressing portion 26 within the body lumen through the long sheath 10 in a state where the pressing portion is contracted, and to expand the pressing portion in the right atrium R. Furthermore, the thrusting portion 27 is thrust into the joint portion between the atrial septum M1 and the foramen ovale valve M2 on which tensile force is exerted in a direction away from each other while pressing the foramen ovale valve M2 in a direction away from the atrial septum M1 using the pressing portion 26. By doing this, the foramen ovale valve M2 is effectively separated from the atrial septum M1 and a foramen ovale O can be favorably formed which is configured such that the foramen ovale valve M2 overlaps the atrial septum M1.

Second Embodiment

A medical device according to a second embodiment is different from the medical device according to the first embodiment only in the configuration of a long (elongated) instrument 120. A detailed description of aspects of this embodiment that are the same as described above will not be repeated.

Figure 32A:
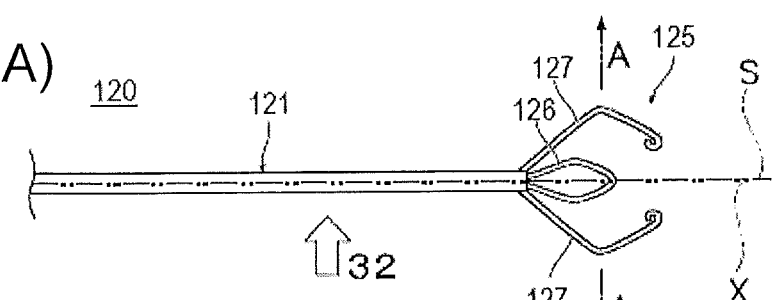

As shown in FIG. 32, the long instrument 120 in the second embodiment includes a shaft portion 121 which is elongated; and a distal end deformation portion 125 which is provided on a distal side of the shaft portion 121 and can be accommodated in the long sheath 10 by being elastically contracted. The distal end deformation portion 125 includes a pressing portion 126 which is annularly formed (i.e., in the shape of a closed loop in the illustrated embodiment) of an elastic material and is interlocked with the shaft portion 121 at a distal end; and two thrusting portions 127 which extend so as to surround the pressing portion 126 from the vicinity of the distal end of the shaft portion 121 using an elastic material. As shown in FIG. 33, the distal end deformation portion 125 can be accommodated in the long sheath 10 through elastic deformation.

As shown in FIG. 33, the pressing portion 126 expands in an expansion direction A intersecting or transverse to a direction of a shaft center (central axis of the shaft) X of a main portion 122, which is formed in a linear shape or a substantially linear shape, of the shaft portion 121 using self-expanding force, by protruding distally beyond the long sheath and being exposed from the inside of the long sheath 10. Similarly, a thrusting portion 127 is also expanded in the expansion direction A intersecting the shaft center X direction of the shaft portion 121 by protruding distally from the long sheath and being exposed from the inside of the long sheath 10. The thrusting portion 127 is more greatly projected than the pressing portion 126 in a direction the same as the expansion direction A of the pressing portion 126 (i.e., the thrusting portion 127 projects further laterally outwardly than the pressing portions 126) and is positioned in a direction different from a direction from the shaft portion 121 to the pressing portion 126 (i.e., the direction from the pressing portions 126 to the thrusting portion 127 is differs relative to the direction from the shaft portion 121 to the pressing portions 126 in plan view as shown in FIG. 32 (B). In the present embodiment, the pressing portion 126 and the thrusting portion 127 are formed of different members from each other each of the pressing portion and the thrusting portion are combined with the distal end of the shaft portion (i.e., the pressing portion 126 and the thrusting portion 127 are both fixed to the shaft portion 121 so that movement of the shaft portion 121 results in movement of the pressing portion 126 and the thrusting portion 127). Here, the fact that the pressing portion and the thrusting portion are formed of different members from each other indicates that the pressing portion and the thrusting portion are not portions with the same member as each other, that is, the pressing portion and the thrusting portion are separated from each other and each of the pressing portion and the thrusting portion is interlocked with the distal end of the shaft portion.

Figure 32B:
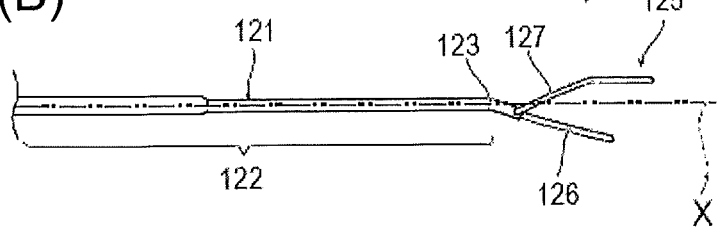

The pressing portion 126 is positioned at a distal portion of the shaft portion 121 away from the shaft center X of the shaft portion 121 due to the formation of a shaft bent portion 123 which is formed so as to be bent in a direction away from the shaft center X of the shaft portion 121 as shown in FIG. 32(B), when being projected onto a reference surface S which is orthogonal to the expansion direction A and passes through the shaft center X of the shaft portion 121 (the distal portion of the shaft portion 121 appears on, or is present on, the reference surface S as shown in FIG. 32 (B) which is a side view). The thrusting portion 127 is formed further or extends further on the distal side than the pressing portion 126 so as to extend to a side opposite to the pressing portion 126 across the shaft center X, when the distal end deformation portion 125 is projected onto the reference surface S (with the distal end deformation portion 125 appearing on the reference surface S as shown in FIG. 32(B) which is a side view). The distal portion of each thrusting portion 127 is curved so as not to cause damage to biological tissues M. The distal end deformation portion 125 is formed in a symmetrical shape with respect to the reference surface S, but may not necessarily be in the symmetrical shape.

The pressing portion 126 and the thrusting portion 127 are elastically deformable wires formed of, for example, a NiTi alloy or the like which is a superelastic material. The shaft portion 121 is formed by, for example, a metal tube, such as stainless steel or the like, and a tube which is formed of resin and a reinforcing material made of metal. The distal end deformation portion 125 is fixed to the shaft portion by caulking the shaft portion in a state where the wire constituting the pressing portion 126 is inserted into the shaft portion. The thrusting portion 127 is joined with the shaft portion 121 through welding or the like. Note that the shaft portion 121 preferably has flexibility to the extent that the shaft portion can move in the curved long sheath 10 and preferably has rigidity to the extent that the distal end deformation portion 125, which is fixed to the distal end of the shaft portion, can be pressed to biological tissues M. In addition, the shaft portion 121 may not be the tubular body. In addition, the method of joining the shaft portion 121, the pressing portion 126, and the thrusting portion 127 together is not particularly limited. For example, the shaft portion 121, the pressing portion 126, and the thrusting portion 127 may be integrally formed.

Figure 33A:
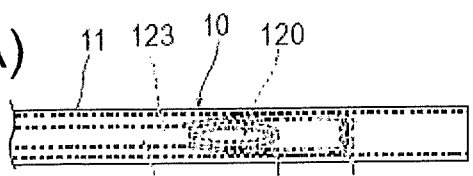
Figure 33B:
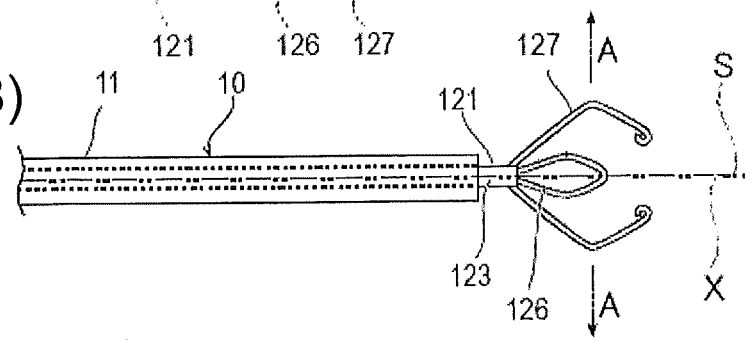

When separating the foramen ovale valve M2 from the atrial septum M1 using the long instrument 120 in the second embodiment, the long instrument 120 is inserted into the sheath portion 11 through the valve body 13 which is provided in the hub portion 12 of the long sheath 10 which has reached the right atrium R. Accordingly, the shaft bent portion 123, the pressing portion 126, and the thrusting portion 127, which are being bent, deform so as to extend in a substantially linear shape and are accommodated in the sheath portion 11 as shown in FIG. 33(A). Then, when an operator presses the shaft portion 121 along the long sheath 10, the distal end deformation portion 125 of the long instrument 120 is exposed in the right atrium R by protruding distally from the opening portion on the distal side of the long sheath 10. Then, as shown in FIG. 33(B), the pressing portion 126 and the thrusting portion 127 are expanded in the expansion direction A intersecting or transverse to the shaft center (central axis of the shaft) X direction of the shaft portion 121 and the shape of the shaft bent portion 123 returns to its bent shape, and therefore, is restored to its original shape using self-restoring force.

Figure 34:
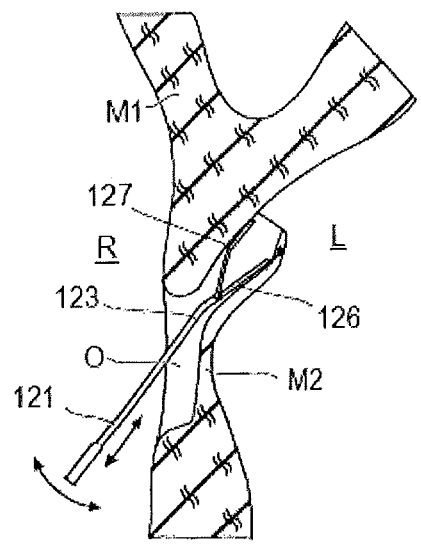
FIG. 34 is a schematic cross-sectional view showing a state when the long instrument in the second embodiment is thrust between the atrial septum and the foramen ovale valve.

Next, as shown in FIG. 34, the pressing portion 126 is abutted on the foramen ovale valve M2 and the thrusting portion 127 is thrust into the joint portion between the atrial septum M1 and the foramen ovale valve M2 while pressing the foramen ovale valve M2 to the left atrium L side using the pressing portions 126. At this time, the shaft portion 121 hardly comes into contact with the foramen ovale valve M2 due to the provision of the shaft bent portion 123, which is formed so as to be bent in the direction away from the shaft center X of the shaft portion 121, on the proximal side of the pressing portion 126 which is positioned away from the shaft center X of the shaft portion 121, and therefore, it is possible to effectively press the foramen ovale valve M2 to the left atrium L side, that is, in a direction away from the atrial septum M1.

In addition, the thrusting portion 127 is positioned in a direction different from a direction in which the pressing portion 126 is positioned, with respect to the shaft portion 121. Therefore, when the foramen ovale valve M2 is pressed to the left atrium L side using the pressing portion 126, it is rather easy to position the thrusting portion 127 further on the right atrium R side than the pressing portion 126, and therefore, it is possible to effectively thrust the thrusting portion into the joint portion between the atrial septum M1 and the foramen ovale valve M2. Then, the thrusting portion 127 is thrust into the joint portion between the atrial septum M1 and the foramen ovale valve M2 on which tensile force is exerted in a direction away from each other while moving the foramen ovale valve M2 in a direction away from the atrial septum M1 by pressing the foramen ovale valve using the pressing portions 126 while applying a forward/backward movement, rotary movement, or the like to the shaft portion 121 depending on the situation. By doing this, the foramen ovale valve M2 is effectively separated from the atrial septum M1 and a foramen ovale O is formed which is configured such that the foramen ovale valve M2 overlaps the atrial septum M1. At this time, the thrusting portion 127 which is formed of a superelastic material is projected in the expansion direction A, and therefore, it is possible to form a foramen ovale O with a predetermined width B in accordance with the width of the thrusting portion 127 in the expansion direction A while applying appropriate force to the expansion direction A. Then, it is possible to exert a larger force on either of the pressing portion 126 or the thrusting portion 127 by making the other side serve as a supporting point, using the principle of a lever.

As in the first embodiment, even if the pressing portion 126 and the thrusting portion 127 are formed of different wires, it is possible to efficiently separate the joint portions from one another by thrusting the thrusting portion 127 into the joint portion of the biological tissues M which are positioned in a direction different from a region to be pressed with respect to the shaft portion 121 while pressing the biological tissues M using the pressing portion 126.

In addition, since the thrusting portion 127 of the distal end deformation portion 125 is formed so as to have a width which becomes narrower toward the distal side, the foramen ovale O becomes larger as the thrusting portion 127 is pressed to the deep portion of the joint portion (i.e., as the thrusting portion is further inserted or moved in the forward direction toward the left atrium L side). Therefore, the size of the foramen ovale O can be adjusted with one instrument, thereby reducing the cost. The width B of the foramen ovale O to be formed is, for example, 5 mm to 20 mm, but the present invention is not limited to this dimensional range.

Third Embodiment

A medical device according to a third embodiment is different from the medical device according to the first embodiment only in the configuration of a long instrument 220. A detailed description of aspects of this embodiment that are the same as in the first embodiment described above will not be repeated.

Figure 37A:
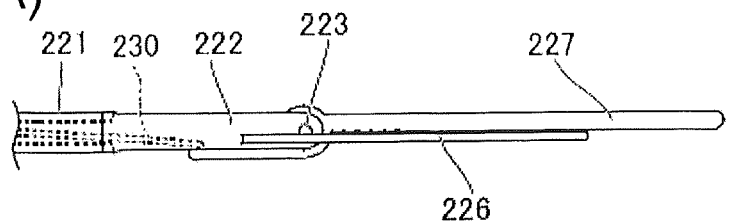
Figure 37B:
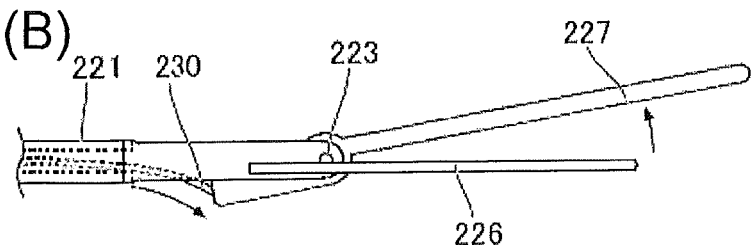

As shown in FIGS. 35 to 37, the long instrument 220 in the third embodiment includes a tubular shaft portion 221 which is elongated; a rotary holding portion 222 which is interlocked with the shaft portion 221 at a distal end of the shaft portion 221 and holds a shaft body 223 that extends in a direction orthogonal to a shaft center (central axis of the shaft) X of the shaft portion 221; a pressing portion 226 which is annularly formed (i.e., in the shape of a closed loop in the illustrated embodiment) from a distal end of the rotary holding portion 222 (or the shaft portion 221), and is expanded in an expansion direction A intersecting or transverse to the shaft center (central axis of the shaft) X direction of the shaft portion 221 by protruding distally from and being exposed from the long sheath 10; and a thrusting portion 227 which is rotatably pivotably attached to the shaft body 223. The long instrument 220 further includes a transmission wire 230 which penetrates or passes through the inside of the shaft portion 221 from the proximal side to the distal side; and an operation member 240 which is provided at a proximal portion of the shaft portion 221 so as to be slidable in the shaft center X direction and with which a proximal portion of the transmission wire 230 is interlocked. The pressing portion 226 is formed in a symmetrical shape with respect to the reference surface S which is orthogonal to the expansion direction A and passes through the shaft center X of the shaft portion 221 but may not necessarily be symmetrical in shape.

The thrusting portion 227 is formed in a substantially linear shape and can be operated like forceps so as to approach and be separated from the pressing portion 226 by rotating around the shaft body 223. A distal portion of the transmission wire 230 is interlocked with the proximal side of the thrusting portion 227, and therefore, it is possible to make the thrusting portion 227 approach and be separated from the pressing portion 226 by rotating the thrusting portion around the shaft body 223 as shown in FIG. 37, by slidingly moving the operation member 240 with which the proximal portion of the transmission wire 230 is interlocked. The thrusting portion 227 can be positioned in a direction different from a direction from the shaft portion 221 to the pressing portion 226, by being separated from the pressing portion 226. Note that in the present embodiment, the pressing portion 226 and the thrusting portion 227 are formed of different members from each other. That is, the pressing portion 226 and the thrusting portion 227 are separate members. In addition, regarding the pressing portion 226 and the thrusting portion 227, when biological tissues are not pressed by the pressing portion 226, the direction from the shaft portion 221 to the pressing portion 226 is the same as a direction from the shaft portion 221 to the thrusting portion 227 (i.e., the direction from the pressing portions 226 to the thrusting portion 227 is same as a direction from the shaft portion 221 to the pressing portions 226 in plan view as shown in FIG. 35 (A)), and when biological tissues are pressed by the pressing portion 226, the direction from the shaft portion 221 to the pressing portion 226 is different from the direction from the shaft portion 221 to the thrusting portion 227 (the direction from the pressing portions 226 to the thrusting portion 227 is different from the direction from the shaft portion 221 to the pressing portions 226 in plan view as shown in FIG. 35 (B)). Here, the fact that the pressing portion and the thrusting portion are formed of different members from each other indicates that the pressing portion and the thrusting portion are not portions with the same member as each other, that is, the pressing portion and the thrusting portion are separated from each other and each of the pressing portion and the thrusting portion is interlocked with the distal end of the shaft portion.

The pressing portion 226 is fabricated as an elastically deformable wire formed of, for example, a NiTi alloy or the like which is a superelastic material. The shaft portion 221 and the thrusting portion 227 are formed by, for example, a metal tube, such as stainless steel or the like, and a tube which is formed of resin and a reinforcing material made of metal. The pressing portion 226 is joined with the rotary holding portion 222 through welding or the like, but the joining method is not particularly limited to such joining. Note that the shaft portion 221 preferably has flexibility to the extent that the shaft portion can move in the curved long sheath 10 and preferably has rigidity to the extent that the pressing portion 226 and the thrusting portion 227, which are provided at the distal end of the shaft portion, can be pressed to or against biological tissues M.

When separating the foramen ovale valve M2 from the atrial septum M1 using the long instrument 220 in the third embodiment, the shaft portion 221, the pressing portion 226, and the thrusting portion 227 are accommodated in the sheath portion 11 in a state of being arranged in a linear shape, through the valve body 13 which is provided in the hub portion 12 of the long sheath 10 which has reached the right atrium R (i.e., is positioned in the right atrium), by making the thrusting portion 227 approach the pressing portion 226 and closing the thrusting portion. Thereafter, when the operator presses the shaft portion 221 along the long sheath 10, the thrusting portion 227 and the pressing portion 226 of the long instrument 220 are exposed in the right atrium R by protruding distally from the opening portion on the distal side of the long sheath 10. Then, the pressing portion 226 is automatically expanded in the expansion direction A.

Figure 38:
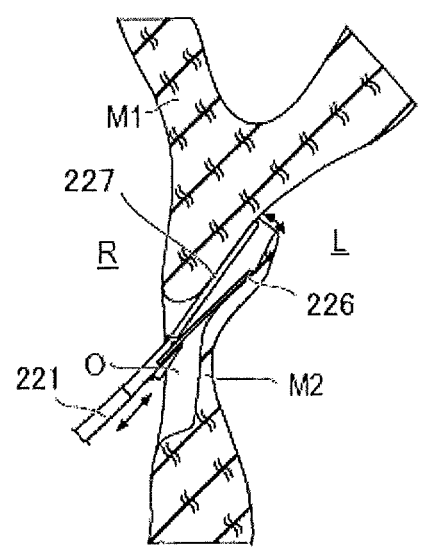
FIG. 38 is a schematic cross-sectional view showing a state when the long instrument in the third embodiment is thrust between the atrial septum and the foramen ovale valve.

Next, as shown in FIG. 38, the pressing portion 226 is abutted on the foramen ovale valve M2 and the thrusting portion 227 is thrust into the joint portion between the atrial septum M1 and the foramen ovale valve M2 while pressing the foramen ovale valve M2 to the left atrium L side using the pressing portion 226. Then, the thrusting portion 227 is separated from the pressing portion 226 through an operation of the operation member 240. Accordingly, tensile force is exerted on the joint portion between the atrial septum M1 and the foramen ovale valve M2 in a direction away from each other and the foramen ovale valve M2 is gradually separated from the atrial septum M1. A forward/backward movement, a rotary movement, or the like is appropriately applied to the shaft portion 221 while repeatedly performing relative opening/closing of the thrusting portion 227 and the pressing portion 226. By doing this, the foramen ovale valve M2 is effectively separated from the atrial septum M1 and a foramen ovale O is formed which is configured such that the foramen ovale valve M2 overlaps the atrial septum M1. At this time, the pressing portion 226 is projected in the expansion direction A, and therefore, it is possible to form a foramen ovale O with a predetermined width B in accordance with the width of the pressing portion 226 in the expansion direction A while applying an appropriate amount of force to the expansion direction A.

According to the medical device in the third embodiment, the pressing portion 226 and the thrusting portion 227 can be opened and closed so as to approach and be separated from each other through an operation of the shaft portion 221 on the proximal side. Therefore, it is possible to exert force on biological tissues M, which are joined together, in a direction in which the biological tissues are separated by the pressing portion 226 and the thrusting portion 227. Therefore, it is possible to effectively separate the joint portions from one another.

In addition, since the pressing portion 226 is formed so as to have a width which becomes narrower toward the distal side, the foramen ovale O becomes larger as the pressing portion is pressed to the deep portion of the joint portion (i.e., the foramen ovale O becomes larger as the pressing portion is moved forwardly into the joint portion). Therefore, the size of the foramen ovale O can be adjusted with one instrument, thereby reducing the cost.

Note that in the third embodiment, the thrusting portion 227 and the pressing portion 226 can be opened and closed by the thrusting portion moving to the pressing portion. However, the present invention is not limited to this as long as the thrusting portion 227 and the pressing portion 226 can be relatively opened and closed. For example, they may be opened and closed by the pressing portion moving to the thrusting portion, or by movement of both of the pressing portion and the thrusting portion. In addition, in the third embodiment, in the pressing portion 226 and the thrusting portion 227, only the pressing portion 226 is formed of a wire which can be expanded and contracted. However, only the thrusting portion 227 may be formed of a wire which can be expanded and contracted, both may be formed of a wire which can be expanded and contracted, or both may not be formed of a wire which can be expanded and contracted.

Fourth Embodiment

Figure 39A:
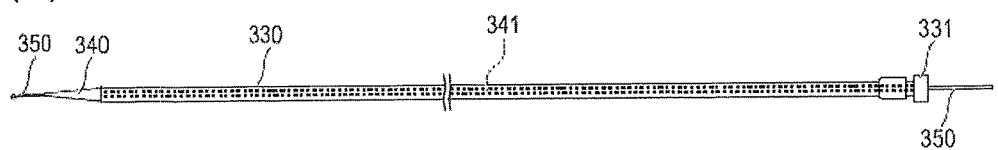
Figure 39B:
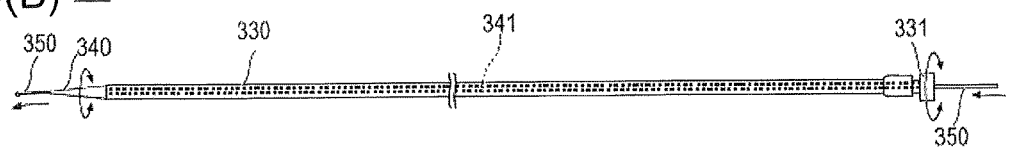
Figure 40:
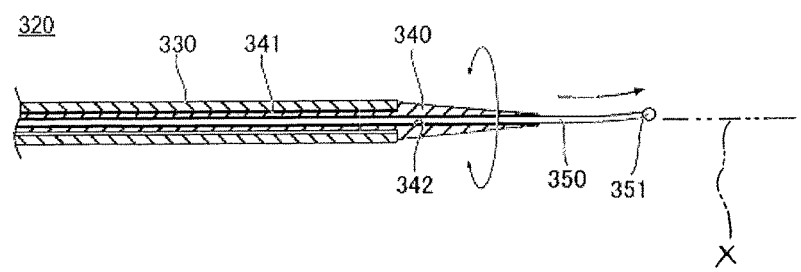
FIG. 40 is a cross-sectional view showing a distal portion of the long instrument in the fourth embodiment.
Figure 41:
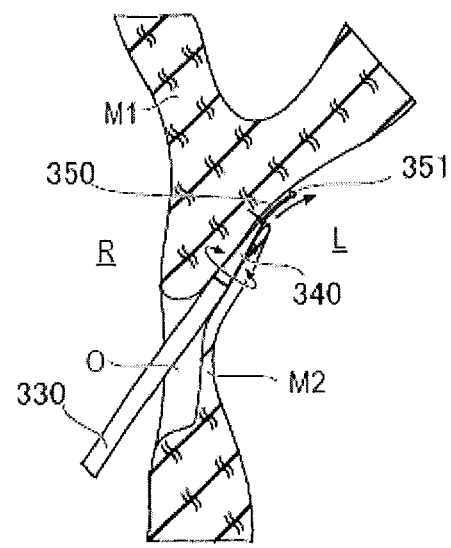
FIG. 41 is a schematic cross-sectional view showing a state when the long instrument in the fourth embodiment is thrust between the atrial septum and the foramen ovale valve.

A medical device according to a fourth embodiment shown in FIGS. 39-41 is different from the medical device according to the first embodiment only in the configuration of a long instrument 320. A detailed description of aspects of this fourth embodiment that are the same as in the first embodiment described above will not be repeated.

The long instrument 320 in the fourth embodiment includes a tubular shaft portion 330 which is elongated; a thrusting portion 340 which is provided on a distal side of the shaft portion 330; a tubular rotational force transmission portion 341 which is accommodated so as to be rotatable in the shaft portion 330 and of which the distal side is interlocked with the thrusting portion 340; and a wire 350 which penetrates the inside of the rotational force transmission portion 341.

The thrusting portion 340 includes a through-hole 342 which communicates with the rotational force transmission portion 341 through a conical shaft center (central axis of the shaft) X, and is provided so as to be rotatable coaxially with the shaft portion 330. The rotational force transmission portion 341 is interlocked with a rotary operation portion 331 which is rotatably provided at a proximal end of the shaft portion 330. Accordingly, it is possible to rotate the thrusting portion 340 through the rotational force transmission portion 341 by rotating the rotary operation portion 331.

The wire 350 penetrates the through-hole 342 of the rotational force transmission portion 341 and the thrusting portion 340, and a distal end-spherical portion 351, which has a size which is not large enough to pass through the through-hole 342, is located at a distal portion of the wire 350.

Examples of the material of the shaft portion 330, the thrusting portion 340, and the rotational force transmission portion 341 include resin which has visibility under X-ray fluoroscopy, resin which is subjected to metal reinforcement, and metal such as stainless steel or the like, but the material is not particularly limited to these materials. The material of the wire 350 is formed of, for example, a NiTi alloy or the like which is a superelastic material, but the material is not particularly limited to such materials. Note that the shaft portion 330 preferably has flexibility to the extent that the shaft portion can move in the curved long sheath 10 and preferably has rigidity to the extent that the thrusting portion 340, which is provided at the distal end of the shaft portion, can be pressed to or against biological tissues M.

When separating the foramen ovale valve M2 from the atrial septum M1 using the long instrument 320 in the fourth embodiment, the long instrument 320 is inserted into the sheath portion 11 through the valve body 13 which is provided in the hub portion 12 of the long sheath 10 which has reached the right atrium R (i.e., is positioned in the right atrium). Then, when an operator presses the shaft portion 330 along the long sheath 10, the thrusting portion 340 of the long instrument 320 is exposed in the right atrium R by protruding distally from the opening portion on the distal side of the long sheath 10.

Next, as shown in FIG. 41, the thrusting portion 340 is thrust into the joint portion between the atrial septum M1 and the foramen ovale valve M2, and a forward/backward movement or the like is appropriately applied to the shaft portion 330 while rotating the thrusting portion 340 by operating the rotary operation portion 331. Then, an operation of pressing the wire 350 is appropriately performed, and opening of a foramen ovale O can be confirmed depending on whether the distal end-spherical portion 351 reaches the left atrium L side. After the distal end-spherical portion 351 reaches the left atrium L side, it is possible to press the thrusting portion 340 to an accurate position using the wire 350 as a guide. Accordingly, the foramen ovale valve M2 is effectively separated from the atrial septum M1 and a foramen ovale O is formed or expanded which is configured such that the foramen ovale valve M2 overlaps the atrial septum M1. At this time, the thrusting portion 340 is in a conical shape, and the foramen ovale O becomes larger as the thrusting portion is pressed to the deep portion of the joint portion. Therefore, the size of the foramen ovale O can be adjusted with one instrument, thereby reducing the cost. Note that the thrusting portion 340 in the present embodiment also functions as a pressing portion that presses the foramen ovale valve M2 to the left atrium L side.

As described above, using the medical device according to the fourth embodiment, it is also possible to efficiently separate the joint portion between the atrial septum M1 and the foramen ovale valve M2 while pressing and thrusting the conical thrusting portion 340 into the biological tissues M. For this reason, it is possible to form a foramen ovale O in biological tissues M without puncturing the biological tissues M and to perform treatment through the foramen ovale O while reducing the influence on a living body.

Note that the present invention is not limited to only the above-described embodiments and various modifications can be made by those skilled in the art within the technical ideas of the present invention. For example, a foramen ovale O is formed in the present embodiments. However, the device and method disclosed here are not limited to forming a foramen ovale O and mat be applied or used in other contexts where there is a separable region in the body lumen. In addition, the specific configurations included in the above-described first to fourth embodiments can be appropriately combined.

The detailed description above describes a medical device and a treatment method. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment method comprising:

percutaneously inserting a medical device into a right atrium in a living body to position a part of the medical device adjacent a foramen ovale valve and an atrial septum in the living body; and separating the foramen ovale valve and the atrial septum from each other using the medical device to form a foramen ovale, wherein the medical device includes a shaft portion which is elongated and possess a central axis, a pressing portion on a distal side of the shaft portion and configured to press biological tissue, and a thrusting portion on the distal side of the shaft portion at a position more distal of the shaft portion than the pressing portion, the thrusting portion being configured to thrust into the biological tissue while the biological tissue is pressed by the pressing portion, in which when pressing the biological tissue using the pressing portion, a direction from the shaft portion to the pressing portion and a direction from the shaft portion to the thrusting portion are different from each other when the pressing portion is pressing the biological tissue, and at least one of the pressing portion and the thrusting portion is configured to be expanded and contracted in an expansion direction that is transverse to the central axis of the shaft portion, the method further comprising moving the pressing portion and the thrusting portion positioned inside a tubular body so that the pressing portion and the thrusting portion protrude distally beyond a distal end of the tubular body, the at least one of the pressing portion and the thrusting portion configured to be expanded and contracted being contracted while positioned in the tubular body and automatically expanding upon being moved to protrude distally beyond the distal end of the tubular body, the pressing portion and the thrusting portion being positioned inside the right atrium when the pressing portion and the thrusting portion are moved to protrude distally beyond the distal end of the tubular body, and the method further comprising thrusting the thrusting portion into a joint portion between the foramen ovale valve and the atrial septum while pressing the foramen ovale valve to a left atrium side using the pressing portion to form the foramen ovale, and performing treatment by percutaneously inserting a treatment instrument that performs the treatment into the left atrium from the right atrium through the foramen ovale, after the separation of the foramen ovale valve and the atrial septum from each other, the left atrium being separated from the right atrium by the foramen ovale valve and the atrial septum.

2. The treatment method according to claim 1, further comprising: joining the foramen ovale valve and the atrial septum to each other by sandwiching the foramen ovale valve and the atrial septum using an electrode, applying electrical energy while the foramen ovale valve and the atrial septum are sandwiched using the electrode, and the joining of the foramen ovale valve and the atrial septum occurring after performing the treatment.

3. The treatment method according to claim 1, wherein the pressing portion and the thrusting portion are constituted by a common member so that one part of the common member is the pressing portion and another part of the common member is the thrusting portion, and a distal end portion of the shaft portion is curved while the pressing portion serves as a fulcrum.

4. The treatment method according to claim 1, wherein the pressing portion and the thrusting portion are formed of different members from each other and are separated from each other in a direction transverse to the expansion direction.

5. The treatment method according to claim 1, wherein the pressing portion and the thrusting portion are formed of an elastically deformable wire.

6. The treatment method according to claim 1, wherein the pressing portion is spaced from a reference plane which is orthogonal to the expansion direction of the pressing portion and contains the central axis of the shaft portion.

7. The treatment method according to claim 1, further comprising moving at least one of the pressing portion and the thrusting portion relative to the other of the pressing portion and the thrusting portion during the separation of the foramen ovale valve and the atrial septum from each other.

8. The treatment method according to claim 1, wherein during the separation of the foramen ovale valve and the atrial septum from each other, when the biological tissue is not pressed by the pressing portion, the pressing portion and the thrusting portion are configured so that the direction from the shaft portion to the pressing portion and the direction from the shaft portion to the thrusting portion are the same.

* * * * *